United States Patent
Troxler et al.

(10) Patent No.: US 8,126,680 B2
(45) Date of Patent: *Feb. 28, 2012

(54) METHODS, SYSTEMS, AND COMPUTER PROGRAM PRODUCTS FOR LOCATING AND TRACKING OBJECTS

(75) Inventors: Robert Ernest Troxler, Raleigh, NC (US); Francois Jacques Malassenet, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/945,822

(22) Filed: Nov. 12, 2010

(65) Prior Publication Data

US 2011/0066398 A1 Mar. 17, 2011

Related U.S. Application Data

(63) Continuation of application No. 11/811,365, filed on Jun. 8, 2007, now Pat. No. 7,848,905, which is a continuation of application No. 11/196,041, filed on Aug. 3, 2005, now Pat. No. 7,786,876, which is a continuation of application No. 10/035,937, filed on Dec. 26, 2001, now Pat. No. 7,034,695, and a continuation-in-part of application No. 10/817,169, filed on Apr. 2, 2004, now Pat. No. 7,376,530, which is a continuation-in-part of application No. 10/269,843, filed on Oct. 11, 2002, now Pat. No. 6,915,216.

(60) Provisional application No. 60/258,246, filed on Dec. 26, 2000.

(51) Int. Cl.
*G06F 17/40* (2006.01)
*G06F 19/00* (2011.01)

(52) U.S. Cl. ........ 702/187; 340/870.07; 702/1; 702/127

(58) Field of Classification Search .................. 340/500, 340/505, 539.1, 539.11, 539.14, 539.16, 340/539.2, 540, 573.1, 578, 579, 686.1, 686.6, 340/870.01, 870.07, 870.16, 870.28, 501, 340/531, 577; 342/350, 352, 356, 357.01, 342/357.06, 357.07, 357.08, 357.09, 357.14; 700/1, 9, 73, 79, 80; 701/200, 204, 205, 701/207, 213; 702/1, 33, 34, 127, 150, 152, 702/187, 188, 189
See application file for complete search history.

(56) References Cited

U.S. PATENT DOCUMENTS 2,883,255 A  4/1959  Anderson
(Continued)

FOREIGN PATENT DOCUMENTS

GB  2 285 135 A  6/1995
(Continued)

OTHER PUBLICATIONS

Notice of Allowance and Fee(s) Due for U.S. Appl. No. 12/179,078 (Jan. 19, 2011).

(Continued)

*Primary Examiner* — Edward Cosimano
(74) *Attorney, Agent, or Firm* — Jenkins, Wilson, Taylor & Hunt, P.A.

(57) ABSTRACT

Methods, systems, and computer program products for locating and tracking objects are disclosed. According to one system, a locating device can be configured to determine a location of an object. According to another system, an identifying device can be configured to determine the identification of an object. Further, a tracking system configured to store tracking information associated with the object. A communications system can be configured to communicate a signal to a remote computer device that identifies the location of the object and includes the tracking information associated with the object.

25 Claims, 25 Drawing Sheets

U.S. PATENT DOCUMENTS

| | | | |
|---|---|---|---|
| 3,534,337 A | 10/1970 | Martin et al. | |
| 4,653,316 A * | 3/1987 | Fukuhara | 73/146 |
| 4,823,366 A | 4/1989 | Williams | |
| 4,965,568 A | 10/1990 | Atalla et al. | |
| 5,132,871 A | 7/1992 | Densham et al. | |
| 5,351,059 A | 9/1994 | Tsuyuki | |
| 5,381,129 A | 1/1995 | Boardman | |
| 5,445,178 A | 8/1995 | Feuer | |
| 5,549,412 A | 8/1996 | Malone | |
| 5,568,119 A | 10/1996 | Schipper et al. | |
| 5,614,670 A | 3/1997 | Nazarian et al. | |
| 5,669,061 A | 9/1997 | Schipper | |
| 5,685,786 A | 11/1997 | Dudley | |
| 5,719,771 A | 2/1998 | Buck et al. | |
| 5,721,685 A | 2/1998 | Holland et al. | |
| 5,742,233 A | 4/1998 | Hoffman et al. | |
| 5,774,876 A | 6/1998 | Woolley et al. | |
| 5,804,810 A | 9/1998 | Woolley et al. | |
| 5,825,283 A | 10/1998 | Camhi | |
| 5,868,100 A | 2/1999 | Marsh | |
| 5,892,454 A | 4/1999 | Schipper et al. | |
| 5,900,736 A | 5/1999 | Sovik et al. | |
| 5,905,461 A | 5/1999 | Neher | |
| 5,947,636 A | 9/1999 | Mara | |
| 5,949,350 A | 9/1999 | Girard et al. | |
| 5,952,561 A | 9/1999 | Jaselskis et al. | |
| 5,959,568 A | 9/1999 | Woolley | |
| 5,959,577 A | 9/1999 | Fan et al. | |
| 5,963,130 A | 10/1999 | Schlager et al. | |
| 5,978,749 A | 11/1999 | Likins, Jr. et al. | |
| 5,982,325 A * | 11/1999 | Thornton et al. | 342/357.31 |
| 5,986,604 A | 11/1999 | Nichols et al. | |
| 6,016,713 A | 1/2000 | Hale | |
| 6,041,582 A | 3/2000 | Tiede et al. | |
| 6,043,747 A | 3/2000 | Altenhofen | |
| 6,043,748 A | 3/2000 | Touchton et al. | |
| 6,072,396 A | 6/2000 | Gaukel | |
| 6,100,806 A | 8/2000 | Gaukel | |
| 6,122,601 A | 9/2000 | Swanson et al. | |
| 6,172,640 B1 | 1/2001 | Durst et al. | |
| 6,225,890 B1 | 5/2001 | Murphy | |
| 6,232,874 B1 | 5/2001 | Murphy | |
| 6,232,880 B1 | 5/2001 | Anderson et al. | |
| 6,236,358 B1 | 5/2001 | Durst et al. | |
| 6,239,700 B1 | 5/2001 | Hoffman et al. | |
| 6,271,757 B1 | 8/2001 | Touchton et al. | |
| 6,301,551 B1 | 10/2001 | Piscalko et al. | |
| 6,320,933 B1 | 11/2001 | Grodzins et al. | |
| 6,353,390 B1 | 3/2002 | Beri et al. | |
| 6,362,778 B2 | 3/2002 | Neher | |
| 6,388,612 B1 | 5/2002 | Neher | |
| 6,421,001 B1 | 7/2002 | Durst et al. | |
| 6,421,608 B1 | 7/2002 | Motoyama et al. | |
| 6,434,372 B1 | 8/2002 | Neagley et al. | |
| 6,441,778 B1 | 8/2002 | Durst et al. | |
| 6,480,147 B2 | 11/2002 | Durst et al. | |
| 6,497,153 B1 | 12/2002 | Hoskinson et al. | |
| 6,518,919 B1 | 2/2003 | Durst et al. | |
| 6,519,530 B2 | 2/2003 | Crockett et al. | |
| 6,520,715 B1 | 2/2003 | Smith | |
| 6,581,546 B1 | 6/2003 | Dalland et al. | |
| 6,624,754 B1 | 9/2003 | Hoffman et al. | |
| 6,700,533 B1 | 3/2004 | Werb et al. | |
| 6,718,248 B2 | 4/2004 | Lu et al. | |
| 6,762,684 B1 | 7/2004 | Camhi | |
| 6,857,016 B1 | 2/2005 | Motoyama et al. | |
| 6,859,171 B2 | 2/2005 | Durst et al. | |
| 6,868,100 B2 | 3/2005 | Larson et al. | |
| 6,892,131 B2 | 5/2005 | Coffee et al. | |
| 6,903,682 B1 | 6/2005 | Maddox | |
| 6,915,216 B2 | 7/2005 | Troxler et al. | |
| 6,919,803 B2 | 7/2005 | Breed | |
| 6,961,659 B2 | 11/2005 | Motoyama et al. | |
| RE38,910 E | 12/2005 | Troxler et al. | |
| 6,995,667 B2 | 2/2006 | He et al. | |
| 7,015,817 B2 | 3/2006 | Copley et al. | |
| 7,034,683 B2 | 4/2006 | Ghazarian | |
| 7,034,695 B2 | 4/2006 | Troxler | |
| 7,038,590 B2 | 5/2006 | Hoffman et al. | |
| 7,113,126 B2 | 9/2006 | Durst et al. | |
| 7,164,986 B2 | 1/2007 | Humphries et al. | |
| 7,171,187 B2 | 1/2007 | Haave et al. | |
| 7,196,621 B2 | 3/2007 | Kochis | |
| 7,236,798 B2 | 6/2007 | Beuck | |
| RE40,073 E * | 2/2008 | Breed | 340/539.14 |
| 7,376,530 B2 | 5/2008 | Bienvenu et al. | |
| 7,385,499 B2 | 6/2008 | Horton et al. | |
| 7,421,334 B2 * | 9/2008 | Dahlgren et al. | 701/117 |
| 7,554,441 B2 | 6/2009 | Viegers et al. | |
| 7,562,563 B2 * | 7/2009 | Wee | 73/104 |
| 7,786,876 B2 | 8/2010 | Troxler | |
| 7,848,905 B2 | 12/2010 | Troxler et al. | |
| 7,920,066 B2 | 4/2011 | Troxler | |
| 7,946,787 B2 * | 5/2011 | Glee et al. | 404/84.8 |
| 2001/0026240 A1 | 10/2001 | Neher | |
| 2001/0053970 A1 | 12/2001 | Ford et al. | |
| 2002/0015354 A1 | 2/2002 | Buckelew | |
| 2002/0032517 A1 | 3/2002 | Buckelew et al. | |
| 2002/0042278 A1 | 4/2002 | Crockett et al. | |
| 2002/0089434 A1 | 7/2002 | Ghazarian | |
| 2002/0152028 A1 | 10/2002 | Motoyama et al. | |
| 2002/0180618 A1 | 12/2002 | Beri et al. | |
| 2002/0196151 A1 | 12/2002 | Troxler | |
| 2003/0050038 A1 | 3/2003 | Haave et al. | |
| 2003/0184450 A1 | 10/2003 | Muller et al. | |
| 2003/0227382 A1 | 12/2003 | Breed | |
| 2004/0021573 A1 * | 2/2004 | Hoffman et al. | 340/573.1 |
| 2004/0041706 A1 | 3/2004 | Stratmoen et al. | |
| 2004/0073382 A1 | 4/2004 | Troxler et al. | |
| 2004/0128613 A1 | 7/2004 | Sinisi | |
| 2004/0260504 A1 | 12/2004 | Bienvenu et al. | |
| 2005/0035865 A1 | 2/2005 | Brennan et al. | |
| 2005/0046584 A1 | 3/2005 | Breed | |
| 2005/0065711 A1 * | 3/2005 | Dahlgren et al. | 701/117 |
| 2005/0066912 A1 | 3/2005 | Korbitz et al. | |
| 2005/0068169 A1 | 3/2005 | Copley et al. | |
| 2005/0114015 A1 | 5/2005 | Motoyama et al. | |
| 2005/0143909 A1 | 6/2005 | Orwant | |
| 2005/0150278 A1 | 7/2005 | Troxler et al. | |
| 2005/0159883 A1 | 7/2005 | Humphries et al. | |
| 2005/0210131 A1 | 9/2005 | Motoyama et al. | |
| 2005/0253703 A1 | 11/2005 | He et al. | |
| 2005/0267700 A1 | 12/2005 | Gamache et al. | |
| 2006/0027185 A1 | 2/2006 | Troxler | |
| 2006/0041380 A1 | 2/2006 | Motoyama et al. | |
| 2006/0063540 A1 | 3/2006 | Beuck | |
| 2006/0145837 A1 | 7/2006 | Horton et al. | |
| 2006/0187026 A1 | 8/2006 | Kochis | |
| 2006/0220842 A1 | 10/2006 | Breed | |
| 2007/0021100 A1 | 1/2007 | Haave et al. | |
| 2007/0026842 A1 | 2/2007 | Haave et al. | |
| 2007/0146163 A1 | 6/2007 | Annoni et al. | |
| 2007/0149184 A1 | 6/2007 | Viegers et al. | |
| 2007/0171047 A1 | 7/2007 | Goodman et al. | |
| 2007/0229350 A1 | 10/2007 | Scalisi et al. | |
| 2008/0004798 A1 | 1/2008 | Troxler et al. | |
| 2008/0088441 A1 | 4/2008 | Breed | |
| 2008/0094212 A1 | 4/2008 | Breed | |
| 2008/0184785 A1 * | 8/2008 | Wee | 73/104 |
| 2008/0262780 A1 | 10/2008 | Bienvenu et al. | |
| 2008/0278309 A1 | 11/2008 | Troxler | |
| 2009/0109040 A1 | 4/2009 | MacLean, III et al. | |
| 2009/0160675 A1 * | 6/2009 | Piccinini et al. | 340/905 |
| 2009/0324331 A1 * | 12/2009 | Glee et al. | 404/75 |

FOREIGN PATENT DOCUMENTS

| | | |
|---|---|---|
| WO | WO 01/11897 A2 | 2/2001 |
| WO | WO 01/73466 A1 | 10/2001 |
| WO | WO2005040847 | 6/2005 |

OTHER PUBLICATIONS

Non-Final Official Action for U.S. Appl. No. 12/123,242 (Dec. 22, 2010).

Supplemental notice of Allowability for U.S. Appl. No. 11/811,365 (Nov. 2, 2010).

Supplemental Notice of Allowability for U.S. Appl. No. 11/811,365 (Sep. 27, 2010).

Final Official Action for U.S. Appl. No. 12/179,078 (Aug. 25, 2010).
Notice of Allowance and Fee(s) Due for U.S. Appl. No. 11/811,365 (Jul. 27, 2010).
Final Official Aciton for U.S. Appl. No. 12/123,242 (May 25, 2010).
Notice of Allowance and Fee(s) Due for U.S. Appl. No. 11/196,041 (Apr. 2, 2010).
Declaration of Robert Troxler in Support of IDS for U.S. Appl. No. 11/196,041 (Feb. 19, 2010).
Non-Final Official Action for U.S. Appl. No. 12/179,078 (Jan. 5, 2010).
Tyson, "How Encryption Works," computer.howstuffworks.com/encryption.htm/printable (Copyright 1998-2010).
Non-Final Official Action for U.S. Appl. No. 11/811,365 (Nov. 25, 2009).
Notice of Allowance and Fee(s) Due for U.S. Appl. No. 11/196,041 (Nov. 9, 2009).
Non-Final Official Action for U.S. Appl. No. 12/123,242 (Jun. 30, 2009).
Stock, "Device Can Track Your Stray Pet," .newsobserver.com/business/story/1476734.html (Apr. 8, 2009).
Non-Final Official Action for U.S. Appl. No. 11/196,041 (Mar. 17, 2009).
Non-Final Official Action for U.S. Appl. No. 11/811,365 (Mar. 2, 2009).
"Positioning Animals Worldwide, Leading the Next Generation of Pet Protection," Positioning Animals Worldwide, Inc., .com/home.aspx (Copyright 2009).
Notification of Transmittal of the International Search Report and the Written Opinion of the International Searching Authority, or the Declaration for International Application No. PCT/US08/07217 (Sep. 22, 2008).
Final Official Action for U.S. Appl. No. 11/196,041 (Jan. 25, 2008).
Notice of Allowance and Fee(s) Due for U.S. Appl. No. 10/817,169 (Jan. 24, 2008).
Interview Summary for U.S. Appl. No. 10/817,169 (Jan. 22, 2008).
Interview Summary for U.S. Appl. No. 10/817,169 (Jan. 3, 2008).
"GPS Re-Radiating Kits," GPS Networking Online, .gpsnetworking.com/ GPS-re-radiating-kits.asp (Copyright 2008).
"3G Chipstes," .qctconnect.com/products/3g_chipsets.html (Copyright 2008).
"Position-Location Solutions (GPS)," .qctconnect.com/products/position_location.html (Copyright 2008).
Eisenberg, "Think Your Dog is Smart? Its Collar May Be Even Smarter," The New York Times, .nytimes.com/2007/08/05/business/yourmoney/05novel. html?_r=1&ref=business&oref+slogin (Aug. 5, 2007).
Non-Final Official Action for U.S. Appl. No. 10/817,169 (Aug. 3, 2007).
Final Official Action for U.S. Appl. No. 11/196,041 (May 8, 2007).
Final Official Action for U.S. Appl. No. 10/817,169 (Apr. 26, 2007).
Kennedy, "Engineer: GPS Shoes Make People Findable," .wral.com/news/ technology/story /1198063/, pp. 1-6 (Feb. 9, 2007).
Non-Final Official Action for U.S. Appl. No. 10/817,169 (Dec. 11, 2006).
Non-Final Official for U.S. Appl. No. 11/196,041 (May 30, 2006).
Advisory Action for U.S. Appl. No. 10/817,169 (May 10, 2006).
Final Official Action for U.S. Appl. No. 10/817,169 (Jan. 11, 2006).
Kushner, "Location , Location, Location: GPS Games get Players Off Their Couches and Into the Real World," IEEE Spectrum, pp. 62, 64, and 67 (Jan. 2006).
Snell, Gun Dog Supply, http://www.gundogsupply.com/ (Copyright 1972-2006).
"High Accuracy-Nationwide Differential Global Positiion System Program Fact Sheet," .tfhrc.gov/its/ndgps/handgps/03039.htm, pp. 1-3 (Dec. 20, 2005).
Non-Final Official Action for U.S. Appl. No. 10/817,169 (Sep. 22, 2005).
Notice of Allowance and Fee(s) Due for U.S. Appl. No. 10/035,937 (Jul. 5, 2005).
Notice of Allowance and Fee(s) Due for U.S Appl. No. 10/269,843 (Mar. 8, 2005).

Non-Final Officail Action for U.S. Appl. No. 10/035,937 (Dec. 21, 2004).
Interview Summary for U.S. Appl. No. 10/269,843 (Nov. 8, 2004).
Final Official Action for U.S. Appl. No. 10/269,843 (Oct. 6, 2004).
Eisenberg, "For the Fretting Pet Owner, a Wireless Distress Signal," The New York Times, pp. 1-2 (Jul. 15, 2004).
"Virtual Fences to Herd Wi-Fi Cattle," .newscientist.com/news.jsp?id=ns99995079 (Jun. 7, 2004).
Non-Final Official Action for U.S. Appl. No. 10/269,843 (Apr. 20, 2004).
"CDMA vs TDMA," .arcx.com/sites/CDMAvsTDMA.htm (Apr. 15, 2004).
Non-Final Official Action for U.S. Appl. No. 10/035,937 (Jan. 13, 2004).
Chartrand, "A Device to Track Missing People," GlobalPetFinder.com, pp. 1-3 (Copyright 2004).
Markoff, "Apple Co-Founder Creates Electronic ID Tags," The New York Times (Jul. 21, 2003).
Warrior et al., "They Know," IEEE Spectrum, pp. 20-25 (Jul. 2003).
"GPS-MS1E," u-blox AG, www.u-blox.com, pp. 1-2 (Copyright 2003).
Oloufa, "Quality Control of Asphalt Compaction Using GPS-Based System Architecture," IEEE Robotics & Automation Magazine, pp. 29-35 (Mar. 2002).
"Mobile Station Modem for MSM3300™," Qualcomm Incorporated, CDMA Technologies (Aug. 2001).
"Position Location Solutions for WCDMA/GSM/GPRS," Qualcomm Incorporated, CDMA Technologies, .qualcomm.com/cdmatech.com (Aug. 2001).
"Position Location Solutions for cdmaOne™ and 1x for gpsOne Enhanced by SnapTrack™," Qualcomm Incorporated, CDMA Technologies (Jul. 2001).
UNAVCO, .unavco.ucar.edu/science_tech (Jun. 19, 2001).
"MSM3300 Chipset Solution," Qualcomm Incorporated, CDMA Technologies (Jun. 2001).
"MSM3300™ Mobile Station Modem," Qualcomm CDMA Technologies, .cdmatech.com/solutions/products/msm3300.html (Copyright 2001).
"µ-blox GPS-MS1E GPS Receiver Module Based on SiRFstar I/LX™," pp. 1-16 (May 16, 2000).
"Global Position System Overview," .colorado.edu/geography/gcraft/noted/gps/gps_f.html (May 1, 2000).
Joe Mehaffey and Jack Yeazel's GPS Information Website, .joe.mehaffey.com (Copyright 1997-2000).
Drane et al., "Position Systems in Intelligent Transportation Systems," Artech House, pp. 22-25, 260-271, 288-293 (Copyright 1998).
"Global Positioning System Fully Operational," U.S. Coast Gaurd Navigation Center, .navcen.uscg.gov/gps/genninfo/global.htm (Jul. 17, 1995).
Longfoot, "An Automatic Network Travel Time System—ANTTS," Vehicle Navigation and Information Systems Conference, vol. 2, pp. 1053-1061 (Oct. 1991).
Postel, "User Datagram Protocol," RFC 768, pp. 1-4 (Aug. 28, 1980).
GlobalPetFinder (Publication Date Unknown).
"GPIB Tutorial," .hit.bme.hu/~papay/edu/GPIB/tutor.htm (Publication Date Unknown).
"PQI 301 Pavement Quality Indicator," TransTech Systems, Inc. (Publication Date Unknown).
"QA Sampling (Special key)," Troxler, p. 3-24 (publication Date Unknown).

"Offset Menu," Trolxer, pp. 7-2-7-8 (Publication Date Unknown).

"Global Positioning System," hyperphysics.phy-astr.gsu.edu/hbase/gpsrec.html (Publication Date Unknown).

Notification of Transmittal of International Preliminary Report on Patentability for International Application No. PCT/US08/07217 (Jun. 1, 2011).

Communication of European publication number and information on the application of Article 67(3) EPC for European Application No. 08768283.7 (Feb. 10, 2010).

Notice of Allowance and Fee(s) Due for U.S. Appl. No. 12/123,242 (Sep. 27, 2011).

* cited by examiner

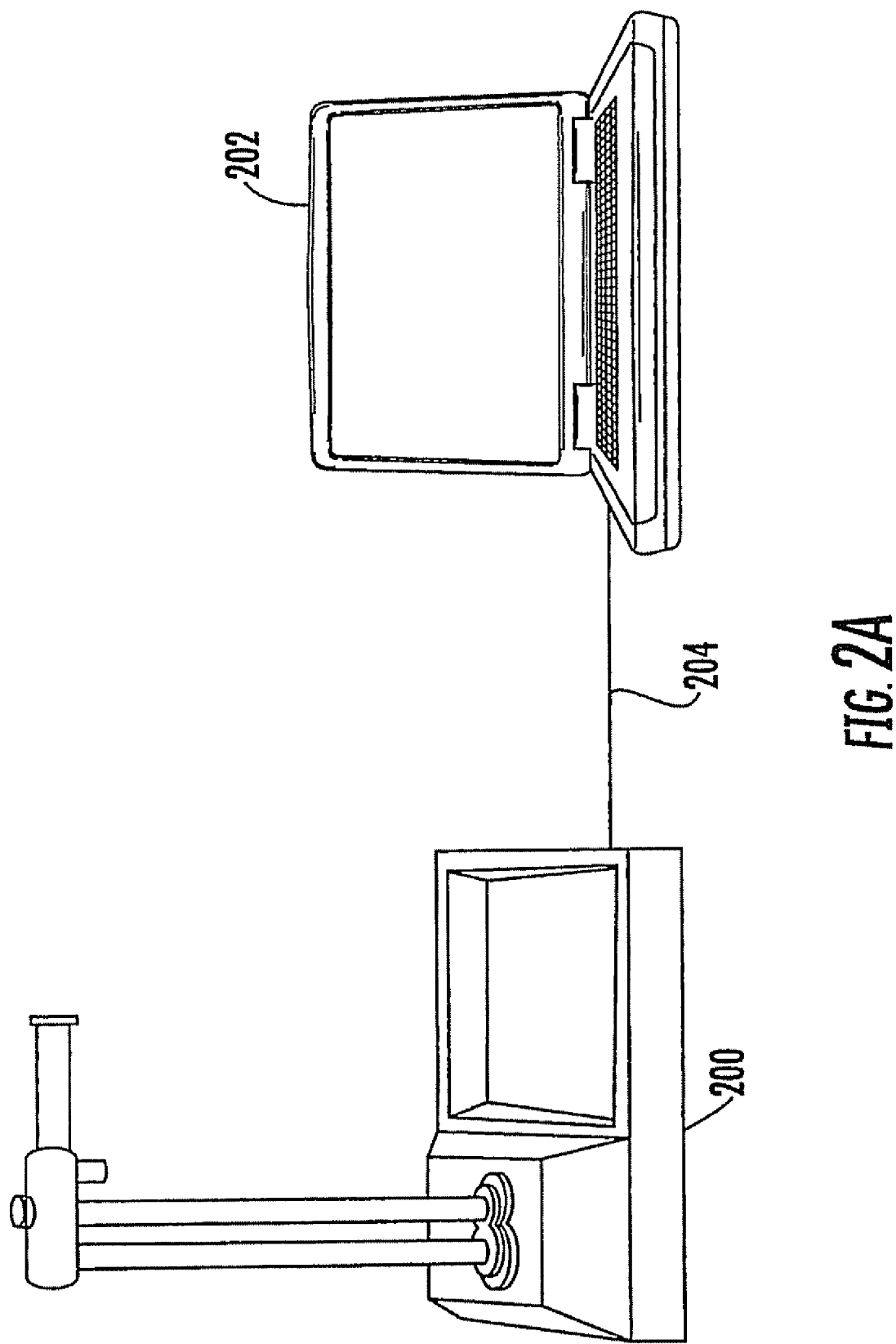

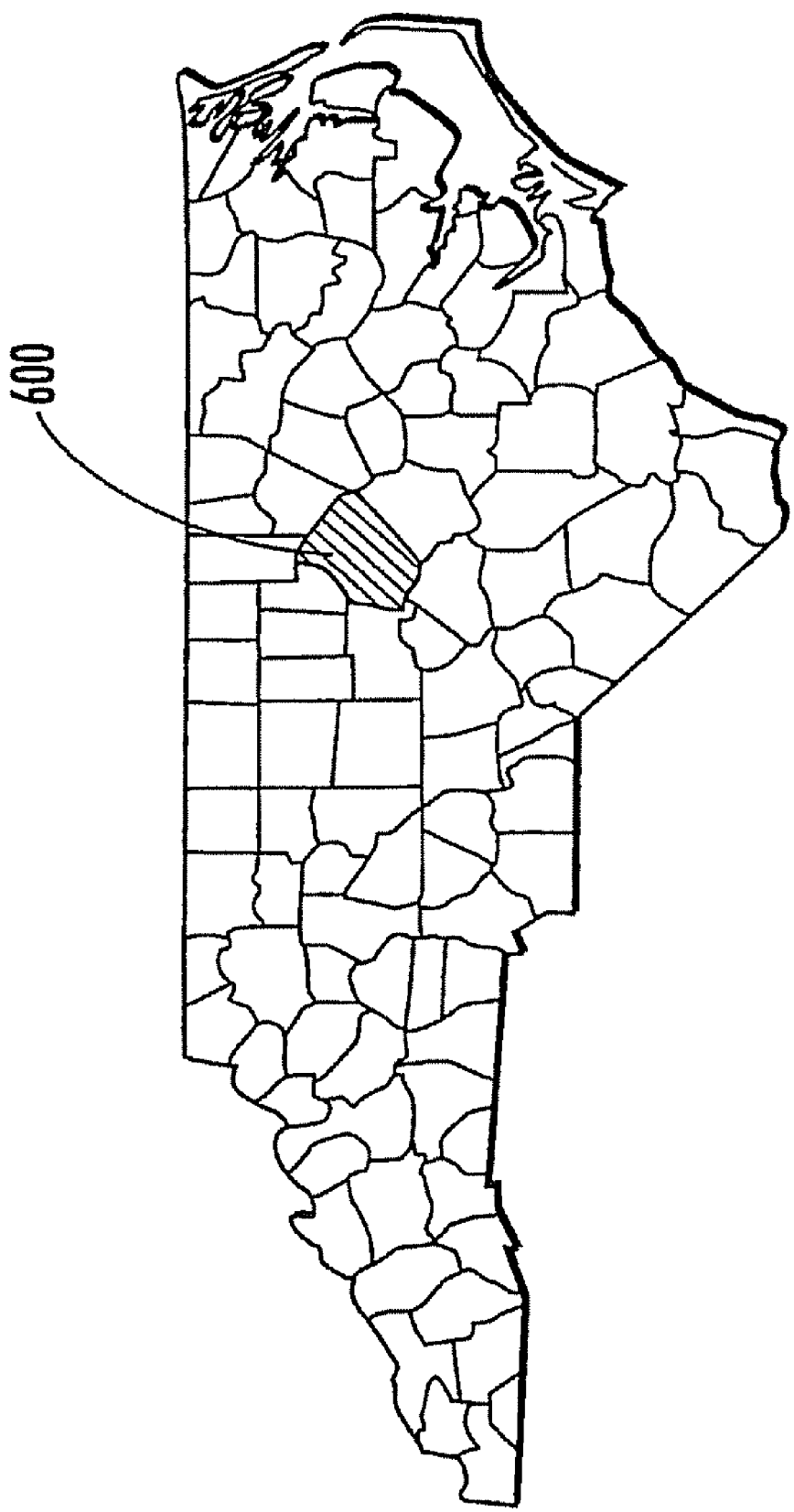

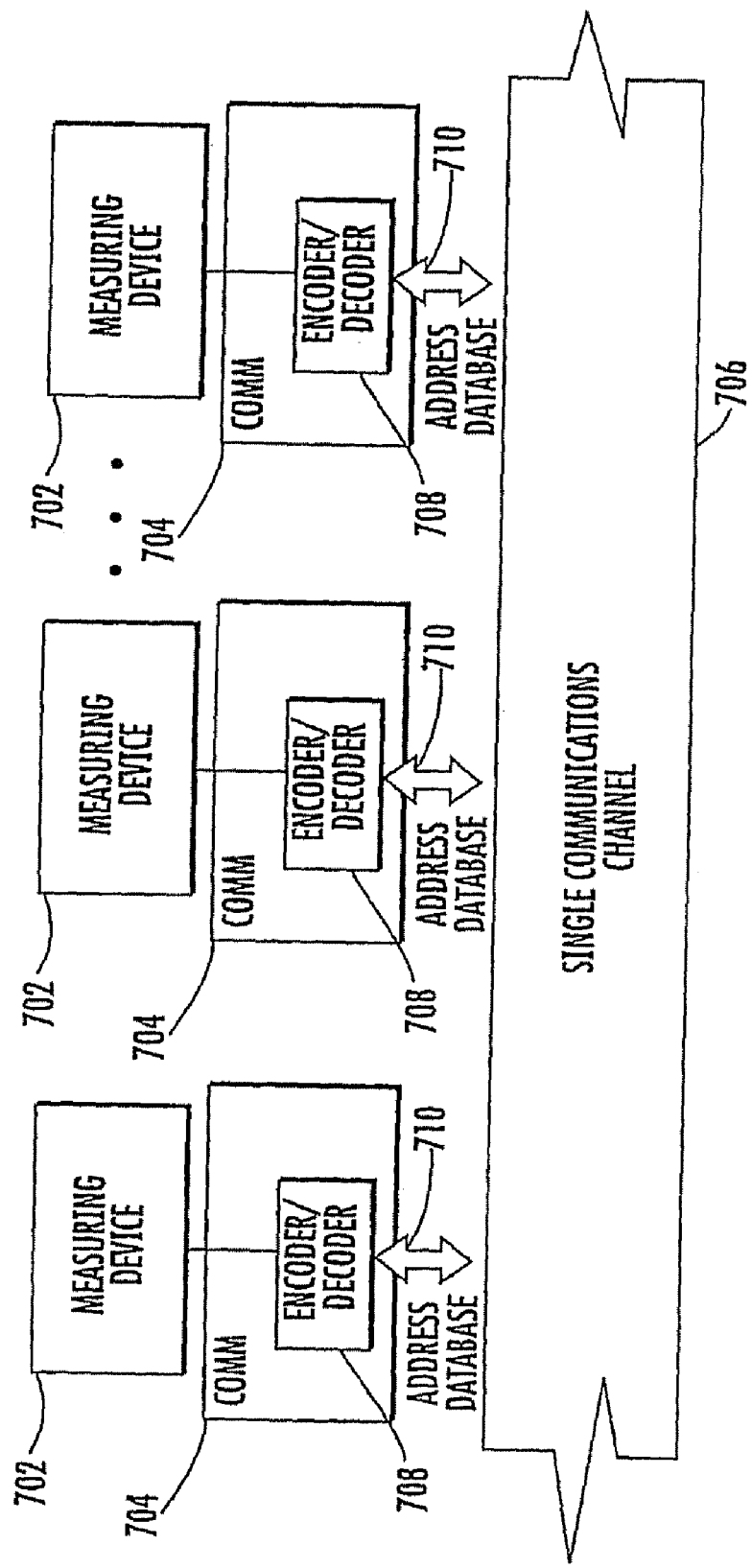

METHODS, SYSTEMS, AND COMPUTER PROGRAM PRODUCTS FOR LOCATING AND TRACKING OBJECTS

RELATED APPLICATIONS

This application is a continuation of U.S. patent application Ser. No. 11/811,365, filed Jun. 8, 2007 now U.S. Pat. No. 7,848,905; which is a continuation of U.S. patent application Ser. No. 11/196,041, filed Aug. 3, 2005 (now U.S. Pat. No. 7,786,876); which is a continuation of U.S. patent application Ser. No. 10/035,937, filed Dec. 26, 2001, now U.S. Pat. No. 7,034,695, which claims the benefit of expired U.S. Provisional Patent Application No. 60/258,246, filed Dec. 26, 2000; and is a continuation-in-part of U.S. patent application Ser. No. 10/817,169, filed Apr. 2, 2004, now U.S. Pat. No. 7,376,530, which is a continuation-in-part of U.S. patent application Ser. No. 10/269,843, filed Oct. 11, 2002, now U.S. Pat. No. 6,915,216; the disclosures of which are incorporated herein by reference in their entireties.

TECHNICAL FIELD

The subject matter described herein relates to methods, systems, and computer program products for locating, identifying, and tracking. More particularly, the subject matter described herein relates to methods, systems, and computer program products for locating, identifying, and tracking an object such as a measuring device.

BACKGROUND

The process of paving roadways is subject to standards which direct the necessary characteristics of the paving used to form the roadway. As such, actual data from the paving contractor supporting such compliance with the applicable standards is often a mandatory requirement of the entity owning the roadway. Often, the entity is part of the government such as, for example, the Department of Transportation of the state. In order to determine compliance with these various standards, the contractor must often perform certain measurements in the field with certain measuring devices at certain points as the roadway is being paved. However, such measuring devices used in the field often use bulky and cumbersome keypads and/or older technology displays having limited capabilities with respect to collecting, storing, manipulating, and displaying the necessary data. In some instances, the measuring device may require the contractor to manually gather the necessary data and/or keep any notes using paper and a writing utensil. The contractor not only must gather the data from the site, but must also transcribe or otherwise manipulate the collected data such that the data can be presented to the owning entity in a usable and/or the required format.

The data collection processes described above are prone to inaccuracies, both in the collection of the data and the transcription and/or manipulation of the data. Such processes may also, in some instances, become more complicated if there is uncertainty between the contractor and the owning entity regarding a measurement location. Accordingly, this may lead to disputes since the owning entity is often not present to actually witness the applicable measurements that are generally manually performed by the contractor. Further, the owning entity typically receives a manually prepared record of the time, date, and location of a measurement as evidence of the contractor's compliance with the applicable standards. Thus, it would be desirable to road paving contractors to have a device for accurately tracking a location of a measuring device and reporting the location to an owning entity.

Further, a nuclear gauge is a measuring device that is routinely used during road paving projects. Nuclear gauges may be used for the determination of certain material properties, such as density and/or moisture content of asphalt paving materials, soil, and concrete. In the pulp and paper industry, nuclear gauges may be used to determine liquid level, moisture and density of liquid mixtures, pulp and raw wood. In metal industries, nuclear gauges may be used to determine metal thickness, metal composition, and metal content in paint such as lead.

Typically, nuclear gauges include one or more radioactive sources. Regulatory agencies typically require that nuclear gauges be routinely monitored to protect against mishandling, theft, and inadvertent loss or control that can occur. Thus, for these additional reasons, it is desirable to provide techniques for tracking a location of a measuring device such as a nuclear gauge, or any object desirous to be tracked such as expensive instruments based on other technologies like electromagnetism, acoustics, optical and such. Other equipment that may require tracking includes medical and scientific instrumentation that contain radioactive material or hazardous material.

In view of the desirability to track measuring devices, there exists a need for improved methods, systems, and computer program products for tracking a location of a measuring device and reporting the location to an entity remote from the measuring device.

SUMMARY

According to one aspect, the subject matter described herein includes methods, systems, and computer program products for locating and tracking an object. One system includes a locating device configured to determine a location of an object. The system can also include a tracking system configured to store tracking information associated with the object. A communications system can be configured to communicate a signal to a remote computer device that identifies the location of the object and includes the tracking information associated with the object. Information can also be stored internally to be downloaded at a later time. A security system incorporating Radio Frequency Identification (RFID) functionality may be utilized for identification purposes.

According to another aspect, the subject matter described herein includes methods, systems, and computer program products for positioning measurement locations of a sample. One system includes a measuring device configured to determine a property of a sample. The system can also include a locating device configured to determine a location of the measuring device. Further, the system can include a computer device operably engaged or not operably engaged with the locating device and configured to indicate one or more locations to position the measuring device for determining the property of the sample. The system can also include a user interface operably engaged with the computer device and configured to present to an operator the information indicating the one or more locations for positioning the measuring device, or simply record the position along with a measurement. Suitable interfaces can include a keypad, PDA, laptop computer, wired or wireless communications, LCD, CRT, and LED.

The methods systems products can be applied to quality control instrumentation to allow location, tracking, detection, identification, and measurements. Other applications can include security monitoring of hazardous materials and containers.

The subject matter described herein can be implemented as a computer program product comprising computer executable instructions embodied in a non-transitory computer readable medium. Exemplary non-transitory computer readable media suitable for implementing the subject matter described herein include disk memory devices, chip memory devices, application specific integrated circuits, and programmable logic devices. In addition, a computer program product that implements the subject matter described herein may be located on a single device or computing platform. It can perform autonomously or by remote control. Alternatively, the subject matter described herein can be implemented on a computer program product that is distributed across multiple devices or computing platforms.

BRIEF DESCRIPTION OF THE DRAWINGS

Exemplary embodiments of the subject matter will now be explained with reference to the accompanying drawings, of which:

FIG. 2A is a schematic view showing more detail of a measuring/locating/tracking device and a computer device according to an embodiment of the subject matter described herein;

FIG. 6 is a geographic map showing an exemplary boundary for a nuclear gauge or hazardous material container;

FIGS. 7A and 7B are schematic diagrams of exemplary modulating/demodulating systems in accordance with the subject matter described herein;

DETAILED DESCRIPTION

Figure 1:
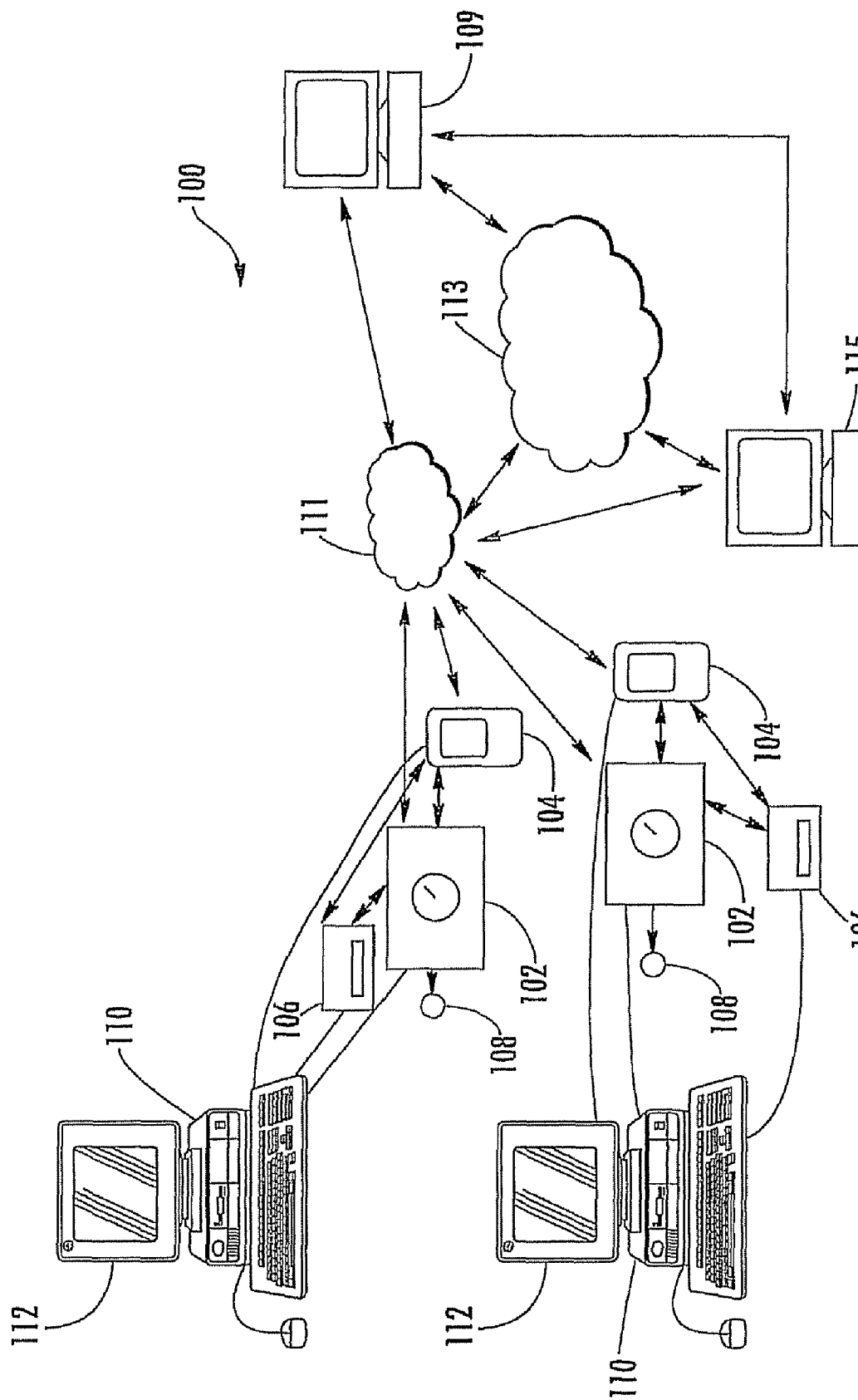
FIG. 1 is a schematic view of an exemplary system for locating and tracking a measuring device and identifying the location to a computer device remote from the measuring device in accordance with the subject matter described herein.

The subject matter described herein includes methods, systems, and computer program products for measuring, locating, identifying, and tracking an object. According to one aspect, the system may include a locating device configured to determine a location of an object, such as a measuring device. The locating device may be positioned near or mounted to the object. Additionally, an identification device may be attached to the object. Further, the system may include a tracking system configured to store tracking information associated with the object. The tracking information may include identification information associated with the object. Further, the tracking information may include routing information for defining a predetermined route for moving the object and/or boundary information for defining a predetermined boundary for the object. The system may also include a communications system configured to communicate a signal to a remote computer device that identifies the location of the object and includes the tracking information associated with the object. The signal may be communicated over any suitable wireless network and/or wireline network. Tracking can also store position coordinates internally to be downloaded at a later time.

As used herein, an "object" refers to any suitable object that may be repositioned or moved. For example, the object may be a measuring device, a vehicle, construction equipment, electronic instrumentation, or cargo. In another example, the object may include a radioactive source, such as a nuclear gauge, medical or scientific instrumentation, products or byproducts. Other exemplary objects include hazardous materials, such as spent nuclear fuel rods and the like, medical waste, biological toxins, and poisonous substances.

As used herein, a "measuring device" refers to any suitable device for measuring one or more properties of a material or sample. For example, a measuring device may be configured to measure a property of a paving-related material. Exemplary properties of a paving-related material include a density, a density-related parameter, modulus, stiffness, strength, cement ratio, permeability, permittivity, and/or a moisture content of at least a soil, an aggregate, concrete, and an asphalt paving mix. Exemplary measuring devices include a nuclear density gauge, a nuclear moisture gauge, a microwave moisture gauge, a TDR moisture and/or density gauge, a frequency domain electromagnetic moisture and/or density gauge, a seismic pavement analyzer (SPA), a portable SPA (PSPA), a stiffness gauge, a falling weight deflectometer, a ground penetrating radar (GPR) type instrument, a radio frequency (RF) device, an electromagnetic device, a microwave device, an acoustic device, a moisture measuring device, a surface roughness measuring device, a pavement temperature sensor, a pavement temperature measuring device, pavement roughness measuring device, soil composition property device, pavement thickness device, a roof moisture device, and combinations thereof. Other exemplary measuring devices may include any suitable instrumentation capable of determining density such as various electromagnetic, acoustic, vibration, and/or microwave based devices. Such measuring devices may be generally directed to measuring density-related parameters such as, for example, a modulus of elasticity (shear and Young's), a stiffness of the soil or asphalt sample, soil strength, a void content, dispersive dielectric property, and bulk density, wherein the determination of such density-related parameters will be readily appreciated by those of skill in the art. Other examples include hand held monitors or personal dosimeter devices. Further, a measuring device may comprise any other suitable field or laboratory device, or combinations thereof, capable of performing the desired property measurements of such paving-related materials.

In one embodiment, the location/communication device can be attached to a moisture measuring microwave instrument for soils and aggregates in cement plants similar to the well known "Ready Mix" facilities. In one example, communication between the sand bin and the computer controlling the hopper is a wireless connection. Some examples of the wireless connection include Bluetooth or WiMax wireless communications techniques. Many plants are portable and can be moved fairly quickly depending on where the cement is needed for a particular project. For instance, when building a concrete airfield or highway, the cement plant is installed nearby. With GPS attached to the actual hoppers, a reading of the location can be included with the aggregate type, operator ID, time date and other information is obtained along with the properties of the material such as moisture, density, cement ratio, and additive quantity. As the aggregate flows near the microwave sensor, measurements are obtained and transferred to the control house or database wirelessly via RF or optical communications. Linking the location as well as the material measurement can be useful for management. Furthermore, this can remove the cumbersome cables currently necessary that must be pulled through conduit at the plant optionally including GPS. As used herein, a "locating device" refers to any suitable device for determining a location of an object. The object may be the locating device itself or another object attached to the locating device or remote from the locating device. Location can be relative and orientated with respect to a marker, beacon, bearing with respect to some base. In one example, a locating device may be operable with one or more of the following for determining a location of an object: a geographic information system (GIS), a global positioning system (GPS), a nationwide differential global positioning system (NDGPS), a high accuracy-nationwide differential global positioning system (HA-NDGPS), a global navigation satellite system (GLONASS), and the European satellite system Galileo. In another example, the locating device may include one or more of the following components for determining a location of an object: dead reckoning components, wave propagating components, accelerometers, magnetometers, gyroscopes, optical or mechanical, RF components, and combinations thereof. Further, a locating device can include mobile communications-based equipment (e.g., cellular telephone technology) adapted for determining an object location. Computer program products incorporating GOOGLE™ maps (available from Google, Inc., of Mountain View, Calif.) or mashmaps can result in visual mapping aids.

In another example of a locating device as described herein, a locating device can include self-positioning functionality and/or remote positioning functionality. A self-positioning system may include components for determining a position of an object without the support of remote components. A remote-positioning system can be operable with a central operations center that determines a location of an object. A self-positioning system can function as a remote-positioning system if each object transmits its position to a central operations center using mobile communication links. An indirect self-positioning system includes a central operations center operable to transmit location information to each sensor in a field.

In another example of a locating device as described herein, a locating device can be operable in a signpost system environment wherein an object can be located in proximity to a location/position reference point known as a "signpost". A signpost location can be measured by attaching a radio frequency (RF) tag to an object to be located. A signpost-based system can be self-positioning in the case that an object has an RF tag attached thereto and is operable to receive a beacon signal. Alternatively, such proximity systems can be implemented using a satellite-based location system, such as GPS. In the case of self-positioning with regard to GPS, a beacon signal can provide an identification code for a local signpost. Alternatively, a satellite signal representing the point of location of a stationary signpost can provide an identification code for a "local" but virtual signpost. By using a lookup database, information from a GPS "signpost" can be communicated to an object, which can be forwarded by the object to a central operations center. Thus, a remote signpost system can include receiving tag-based information at an object from a virtual signpost, which can be forwarded by the object to a central operations center.

Further, the subject matter described herein includes methods, systems, and computer program products for positioning measurement locations of paving-related material. The system may include a measuring device configured to determine a property of a paving-related material. Further, the system may include a locating device configured to determine a location of the measuring device. The system may also include a computer device operably engaged with the locating device and configured to indicate one or more locations to position the measuring device for determining the property of the paving-related material. The computer device may indicate a location to position the measuring device based on a location at which a property of a paving-related material is to be determined. Further, the system may include a user interface operably engaged with the communications system and configured to present to the operator the information indicating and guiding to operator to the one or more locations for positioning the measuring device. The operator may position the measuring device at the locations indicated by the user interface.

As used herein, a "user interface" may be any suitable device, component, and/or system for presenting information to an operator and/or receiving input from an operator. Exemplary user interfaces include a graphical user interface (GUI), a display, a touch screen display, a keyboard, a keypad, a CRT, a projector, a mouse, a trackball, a printer, a speaker, and a scanner. The GUI may not need to be operably engaged with either the measuring device or the location device. The user interface may be configured to present information to an operator that indicates a location of the measuring device. In one example, the user interface may be configured to present to an operator an actual location of the measuring device. In another example, the user interface may be configured to present to an operator a location of the measuring device with respect to a boundary, route, and/or other location. In another example, the user interface may be configured to present to an operator one or more locations and/or measurement results of the measuring device over a period of time and/or associated one or more locations of the measuring device with a time stamp indicating when a measurement was taken by the measuring device at the location. In another example, the user interface can present to the operator vectors to a location of measurement.

FIG. 1 illustrates a schematic view of an exemplary system 100 for locating and tracking a measuring device and identifying the location to a computer device remote or connected to the measuring device in accordance with the subject matter described herein. Referring to FIG. 1, system 100 may include one or more measuring devices 102 and corresponding locating devices 104 and tracking systems 106. Time stamps may be retrieved from the global positioning device, internal clock, cellular telephone system, or even a national broadcast. Measuring device 102 can be configured to measure the property of a sample 108. For example, measuring device 102 can measure a property of a paving-related material such as asphalt paving mix, a soil, or an aggregate. In one example, measuring device 102 may include a nuclear gauge such as, for instance, a Model 3440 Plus Nuclear Density Gauge (available from Troxler Electronic Laboratories, Inc. of Research Triangle Park, North Carolina) for determining a density of sample 108. In another example, measuring device 102 may include a Model 4300 Moisture Meter (available from Troxler Electronic Laboratories, Inc.) or microwave based instrument for determining the moisture content of sample 108. Other instruments include electromagnetic TDR moisture and density meters available from Geodurham, capacitive asphalt quality meters such as the PQI from Trans Tech systems, the electromagnetic asphalt density meter Pavetracker (available from Troxler Electronic Laboratories, Inc., of Research Triangle Park, North Carolina), multiband frequency swept soil/asphalt analysis devices, seismic modulus systems, pentrometers, stiffness gauge by Humboldt, BCD, portable FWD movable FWD's and the like.

System 100 may also include a computer device 110 having a user interface 112. Computer device 110 is a personal computer (PC). Alternatively, computer device 110 may be a mobile phone, a personal digital assistant (PDA), a personal navigation device (PNA), a notebook computer, a personal communications device, a custom configured controller, or any other suitable computing device, such as a "smart device" or the like. User interface 112 is a display configured to present information to an operator. Alternatively, computer device 110 may be any other suitable user interface for presenting information to an operator and receiving input from the operator. Further, computer device 110 can be operably engaged with measuring device 102, locating device 104, and/or tracking system 106. In one example, the functionality of device 102, locating device 104, tracking system 106, and computer device 110 can be at least partially or entirely contained in a single device, such as device 102. An operator can input commands into computer device 110 for operating and monitoring measuring device 102, locating device 104, and/or tracking system 106. Further, computer device 110 can receive information from measuring device 102, locating device 104, and/or tracking system 106, analyze the information, and present the information and its analysis to the operator via user interface 112. For example, computer device 110 can receive sample measurement data from measuring device 102, analyze the sample measurement data, and present the measurement data and its analysis to an operator via user interface 112. In another example, computer device 110 can receive position/location information from locating device 104, analyze the position/location information, and present the position/location information and its analysis to an operator via user interface 112. In yet another example, computer device 110 can receive tracking information from tracking system 106, analyze the tracking information, and present the tracking information and its analysis to an operator via user interface 112. In another example, computer device 110 may also receive a combination of information from measuring device 102, locating device 104, and/or tracking system 106, analyze the information, and present the information and its analysis to an operator via user interface 112. Measuring device can have locating device, programming device, microcomputer or microcontroller integrated thereof for stand alone autonomous operation.

Locating device 104 may be operably engaged with measuring device 102. Further, locating device 104 may include, for example, a GPS device or other satellite and/or land-based beacon type of locating device implementing, in some instances, a location enhancement scheme such as Differential GPS (DGPS), pseudolites, or a Wide Area Augmentation Scheme (WAAS) and RTK. Other exemplary methods that can improve the GPS system include enhancement with the cellular network, inertial and compass augmentations, or techniques to determine elevation, altitude and direction.

Tracking system 106 may be configured to store tracking information associated with one or more measuring devices 102. Further, tracking system 106 may include hardware, software, and/or firmware components for storing and managing tracking information associated with one or more measuring devices 102. In one example, tracking system 106 may store and manage tracking information for its corresponding measuring device 102. In another example, tracking system 106 may store and manage tracking information for any of measuring devices 102. In one example, the tracking information may include information for identifying measuring device 102. In another example, the tracking information may include hazardous material identification information for identifying hazardous material contained in measuring device 102, such as in the case of the measuring device being a nuclear gauge containing radioactive material. Other hazardous materials or items that require tracking may include biohazardous materials, hazardous chemicals, and weapons. In one example, tracking system 106 may include only identification processes.

In another example, the tracking information may include boundary information that defines a predetermined boundary for measuring device 102. In this example, the predetermined boundary can be compared to one or more determined positions/locations of measuring device 102 for determining a position/location of measuring device 102 with respect to the predetermined boundary. Tracking system 106 may use the information regarding the position/location of measuring device 102 with respect to the predetermined boundary to determine whether measuring device 102 is within the predetermined boundary. In the event that boundaries are breached, alarms can be activated. The boundaries can be allowed zones or excluded zones.

In yet another example, the tracking information may include routing information that defines a predetermined route for transporting measuring device 102. In this example, the predetermined route can be compared to one or more determined positions/locations of measuring device 102 for determining a position/location of measuring device 102 with respect to the predetermined route. Tracking and location system can be enhanced for accuracy using surveying techniques such as CORS and OPUS. These enhancements and similar end result approaches can be performed in Post Processing algorithms. Real time differential methods relating to beacons or base stations at known locations can also enhance the accuracy of the location readings. Real Time Kinematics (RTK) may also be utilized.

Tracking system 106 may use the information regarding the position/location of measuring device 102 to determine whether measuring device is within the predetermined route and/or moving in accordance with the predetermined route. For example, tracking system 106 may use the position/location information of measuring device 102 and the predetermined route to determine whether the position of measuring device 102 is greater than a predetermined distance from the predetermined route. A remote entity may be notified in response to determining that measuring device is not positioned within the predetermined boundary and/or positioned greater than a predetermined position from the predetermined route. In another example, the time stamp corresponding to a location of the measuring device may be compared to the time included in the route schedule. A remote entity may then be notified in response to determining that measuring device is or is not positioned within the predetermined boundary and or predetermined position for the predetermined route at the proper time or within curfew.

Measuring device 102 may contain hazardous material such as a radioactive material. For example, a nuclear gauge may include radioactive source. The hazardous material may be securely affixed to and/or contained within measuring device 102 in order to prevent the removal and/or tampering of the hazardous material, thus obtaining an indication of the "health" of the system. In one embodiment, measuring device 102 may include a detector configured to determine removal of the hazardous material from measuring device 102 or tampering of the hazardous material. Further, the detector may be configured to indicate tampering or removal of the hazardous material to a user interface associated with measuring device 102 for communication of the tampering or removal to an operator of measuring device 102. The detector may also be configured to indicate tampering or removal of the hazardous material to a communications system associated with measuring device 102 for communication of the tampering or removal to an entity remote from measuring device 102. A measuring device may be attached to hazardous material such as radioactive isotopes, medical waste, chemicals, and thus integrated into an alarm system for indicating tampering or removal. A measuring device can also be an instrument for purposes of use other than a shipping alarm. For example a nuclear density gauge can contain detectors and sources for obtaining properties of construction materials. The detectors can be remotely activated at any time during shipping or other transportation to monitor the status of the radioactive source from a remote location.

Further, an alarm system may be configured to alarm on the determination of the tampering with software and/or data, such as boundary or measurement programs or data. For example, an alarm system may be set by identifying a hacker or other individual attempting to tamper with the software and/or data. In this example, the device may have an alarm state for checking whether there has been unauthorized changes. For example, the alarm state may include checking for software or data corruption. Exemplary check for corruption may include using a hash algorithm, a checksum technique and a cyclic redundancy check (CRC).

In one embodiment, an entity remote from measuring device 102, locating device 104, and/or tracking system 106 may communicate a polling signal to one of measuring device 102, locating device 104, and tracking system 106 for requesting location, identification, and/or tracking information. In one example, the polling signal may include a request for information indicating a current location/position of measuring device 102. In another example, the polling signal may include a request for information indicating a location/position of measuring device 102 with respect to a predefined boundary. In yet another example, the polling signal may include a request for information indicating a location/position of measuring device 102 with respect to a predefined route. In another example, the polling signal may include a request for hazardous material identification information associated with hazardous material of measuring device 102. In response to receiving the polling signal, a communications system associated with measuring device 102, locating device 104, and/or tracking system 106 may retrieve the requested information and communicate the information to the entity requesting the information. The remote entity may receive the requested information and present the information to an operator. The communications can be short range or long range.

According to one embodiment, computer device 110 may be operably engaged with measuring device 102, locating device 104, and/or tracking system 106 and configured to indicate one or more locations to position measuring device 102 for determining a property of sample 108. User interface 112 may be configured to present to an operator the information and/or vectors indicating the locations for positioning measuring device 102. Based on the information, the operator may move measuring device 102 to the indicated locations and input commands for controlling measuring device 102 to obtain a sample measurement.

In one embodiment, computer device 110 is configured to associate a time stamp with a determined property of sample 108 and/or the position/location of measuring device 102 where the measurement of the property was obtained. By time stamping, an operator can be provided with information regarding the timing of property measurements and respective positions/locations of the measurements.

In one embodiment, a communications system may be operably engaged with locating device 104 and configured to communicate to computer device 110 a location/position at which measuring device 102 determined a measurement of a sample. In response to receiving the location information, computer device 110 determines another different location to position measuring device 102 for obtaining another measurement of a sample. For example, computer device 110 may include instructions for obtaining sample measurements at predetermined distances. Based on the location/position of sample measurement indicated by locating device 104, computer device 110 can determine another location/position that is a predetermined distance from the location/position indicated by locating device 104. Computer device 110 can display a map and/or instructions for repositioning measuring device 102 in the other location/position. Measuring device 102 can be positioned in the other location/position by an operator or other suitable technique for acquiring a sample measurement at the location/position.

Computer device 110 may communicate with system 109 via one or more wireless or wireline networks such as networks 111 and 113. For example, the communication may be accomplished via a wide area network (WAN), a local area network (LAN), a satellite network, GSM or GPRS systems, SMS, or over the Internet. Voice/data network protocols and frequencies that may be supported include, but are not limited to, for example, the global system for mobile communications (GSM), general packet radio service (GPRS), dual-mode advanced mobile phone service (AMPS)/circuit switched data and code division multiple access (CDMA/1XRTT) (used, for example, in U.S. PCS cellular telephone systems), TDMA, DataTAC, and Mobitex. Other network protocols and frequencies are known in the art and may be supported as well. For example, emerging technologies such as 4G or the IEEE 802.11 protocol may be implemented or direct communication through BLUETOOTH™ technology may also be used. For transportation related communications, IEEE 1609 WAVE (Wireless Access in Vehicular Environments) standards may be utilized. Further, a conventional telephone system (POTS) may be implemented. As such, the data may be communicated in many different communications options available, wherein the data may be, for example, included in a simple e-mail message, posted on a web page, or supplied in a complex encrypted data stream.

In one embodiment, the GPRS, CDMA, or TDMA wireless wide area network interface allows communication between the computer device 110 and public digital cellular telephone networks. As such, the computer device 110 may be, in some instances, configured as or may include a cellular telephone capable of allowing the user to communicate with other cellular telephones over the public digital cellular telephone networks. Further, with such various communication options available, software updates and/or relevant data for a separate measuring device 102, locating device 104, and tracking device 106 may be readily provided thereto by central computer system 109 or any other authorized computer system associated with, for instance, the manufacturer of the particular component. For example, central computer system 109 may be configured to provide or perform flash upgrades of the software run by the computer device 110. In the alternative, such software and/or data may also be accessed by the computer device 110 at a specific site and then distributed to the measuring device 102, locating device 104, and/or tracking device 106, if necessary.

Computer device 110 may be configured to communicate the collected data with a third party computer device 115 in addition to, or instead of, with central computer system 109 associated with the contractor. For example, third party computer device 115 may be associated with the owning entity and/or the particular state Department of Transportation. In such instances, the data collected from measuring device 102, locating device 104, and tracking device 106 by computer device 110 may be associated with, for example, a time and date stamp, or an electronic identifier for measuring device 102, locating device 104, and tracking device 106 (type and/or serial number), the operator thereof, sample 108, locating device 104, computer device 110 receiving the data and their operator thereof, and/or the contractor, with each sample property/measuring device location measurement performed by the measuring device 102/locating device 104 unit and transmitted to computer device 110. The data may be collected from computer device 110, for example, in real time (as each data element is collected), at the conclusion of a planned series of measurements, at the end of a day, at the end of a job, or on an otherwise periodic basis, and then communicated with third party computer device 115, preferably without allowing the raw data to be altered or otherwise manipulated by the operator of measuring device 102, locating device 104, and tracking device 106 or computer device 110, or by the contractor. For example, the data could be written into a read-only file or the third party could assign a software security key to the data file on computer device 110 so as to deter any tampering with the data written to the file. Also, the data could be encrypted with an embedded authentication method with software security keys on the computer device 110 so as to deter any tampering with the data written to the file. However, in some instances, computer device 110 may be configured to provide a graphic depiction, such as a variety of graphs or graphics, of the data for display to the third party, wherein the graphical depiction would be provided in addition or in the alternative to the untouched raw data.

FIG. 2A illustrates a schematic view showing more detail of a measuring/locating/tracking device 200 and a computer device 202 according to an embodiment of the subject matter described herein. Referring to FIG. 2A, measuring/locating/tracking device 200 may be an integrated unit containing a measuring device, a locating device, and a tracking device as described herein. Computer device 202 may be integrated with or securely attached to measuring/locating/tracking device 200. That is, measuring/locating/tracking device 200 and computer device 202 may be built into a single case or enclosure so as to provide a self-contained device. Computer device 202 may be configured to be in communication with device 200 via a communication element 204. Computer device 202 may be provided in addition to a control system 200 or in the alternative to control system 200.

Communication element 204 may be operably engaged between computer device 202 and measuring/locating/tracking device 200 in many different manners. For example, computer device 202 may be configured to communicate with measuring/locating/tracking device 200, for example, via a communication element configured to use a wireless technology using appropriate wireless transceivers operably engaged with the appropriate component. Exemplary wireless communication technologies that may be used by communication element 204 include analog and/or digital wireless communications systems and/or modulation schemes such as BLUETOOTH™ wireless technology, WIFI, GPRS, GSM, WiMAX, IR, FSK, PSK, radio frequency systems, and the like. Alternatively, communication element 204 may be a wire element (such as a ribbon cable) connecting computer device 202 to device 200. In such instances, for example, the wire element may be configured to be extendable such that computer device 202 may be physically separated from measuring/locating/tracking device 200, but remain in communication therewith via the wire element. Thus, in instances where communication element 204 is embodied in wireless communication technology or a wire element, communication between computer device 202 and device 200 may be selectively established at any time. That is, such communication may be established in preparing or programming computer device 202 in order to, for example, determine one or more parameters affecting the property measurement performed by measuring/locating/tracking device 200. Communication may also be established to, for example, monitor the progress of measurements; control the process, adjust one or more parameters during a measurement process, or to receive measurement data from measuring/locating/tracking device 200. Communications between 202 and 200 can be short (a few meters) or long range (several Km). Another example is that an integrated computer can be removed and data downloaded into a PC or other computer device. For example, model 3450 from Troxler the computer device 202 can be removed from the measurement device 200, taken to another location and downloaded to a PC via RS-232 connection. In the Troxler Electronic Laboratories, Inc.'s Model 3440+, all information is recorded in a USB device which can be removed from device 200 and connected to a PC.

Referring to FIG. 2A, measuring/locating/tracking device 200 may be configured to be in communication with a beacon device, wherein the beacon device may be configured to transmit a signal to measuring/locating/tracking device 200 if it is determined that the device is lost, misplaced, or stolen. In response to receiving the signal, measuring/locating/tracking device 200 can send a signal back to the beacon device indicative of the physical position and/or movement parameters of the unit, as determined by the locating component of measuring/locating/tracking device 200. In other instances, the unit may be configured to send a signal to the beacon device indicative of the physical position and/or movement parameters of the unit if the unit becomes separated from the beacon device by more than a predetermined distance. In this regard, computer device 202 may also be operably engaged or communicable with measuring/locating/tracking device 200 or, in other instances, computer device 202 may have a separate locating device operably engaged therewith. If the communication link between the beacon device and the measurement device were lost, an alarm can be issued.

In instances where computer device 202 is configured to be in wireless communication with measuring/locating/tracking device 200, computer device 202 may be configured to communicate with only a single measuring/locating/tracking device 200 unit, with multiple measuring/locating/tracking device 200 units, and/or with other computer devices 202 configured for a separate set of measuring/locating/tracking device 200 units. In such instances, computer device 202 and/or measuring/locating/tracking device 200 may be configured with appropriate electronic coded keys, such as a Radio Frequency Identification (RFID) tag, or other identifiers so as to ensure that a computer device 202 communicates only with the appropriate measuring/locating/tracking device 200 (and/or other measuring/locating/tracking device 200 units). For example, an identifier may be a digital key for coding a particular measuring/locating/tracking device 200 unit with computer device 202. Examples of RFID devices are the EM1402 RFID tag available from Trossen Robotics, L.L.C., of Westchester, Ill., and the HITAG family of RFID security devices available from NXP Semiconductors Netherlands B.V., of Eindhoven, the Netherlands. Such identifiers may serve other purposes such as, for example, maintaining an inventory of measuring/locating/tracking device 200 units or tracking such units in the field. The key may belong to a series of key or key chains that may be used in symmetrical or asymmetrical encryptions such as public-private key protocols. The encryption technique may enable hierarchal access to measurement/location/tracking downloading and uploading. For example, some keys may enable access to some information/features but some other information/features are not available. Other keys may lead to full access to all information/measurements/tracking.

According to one embodiment, computer device 202 may be configured to collect data from measuring/locating/tracking device 200 unit(s), sometimes in real time, wherein such data includes the measured sample property and the location of measuring/locating/tracking device 200 when or approximately when the sample property is measured thereby. Computer device 202 may also be configured to be capable of performing tasks such as, for example, associating a time and date stamp, or an electronic identifier for measuring/locating/tracking device 200 (type and/or serial number), the operator thereof, and/or the contractor, with each sample property/measuring device location measurement performed by measuring/locating/tracking device 200 unit and transmitted to computer device 202. In other instances, computer device 202 may perform any or all necessary calculations and/or manipulate the data for display to a user, wherein, for example, the raw data could be displayed or the data may be manipulated to produce a variety of graphs and graphics that may be presented to the user on a screen of computer device 202. It is envisioned that several other functionalities may be implemented in computer device 202. For example, computer device 202 may be configured to include digital filtering or other digital signal processing incorporated therewith, or may be configured with many different capabilities for further enhancing the system of measuring/locating/tracking device 200 and computer device 202. Other enhancements include the NOAA OPUS (online positioning user service) and CORS (continuously operating reference station.) Although these services require data to be obtained for extended sessions, they serve as examples of enhancement schemes and algorithms that continue to improve with location technologies.

Each computer device 202 may be configured to communicate collected data with one or more central computer systems 109, wherein system 109 may include, for example, a host system associated with a contractor. System 109 may also be configured to house a database such as, for example, a geographic information system (GIS). One advantage of such a configuration is that the data may be collected at a central repository having a more expansive, secure, reliable, and stable data storage configuration than computer device 202 which may have limited memory and which is subject to a relatively hostile environment in the field. The data may be collected from computer device 202, for example, in real time (as each data element is collected), at the conclusion of a planned series of measurements, at the end of a day, at the end of a job, or on an otherwise periodic basis. System 109 may also have greater computing and analysis capabilities, as well as more extensive data presentation capabilities, for manipulating the collected data, wherein data from many different computer devices 202 and measurement devices 202 may be collected for comprehensive analysis.

Figure 2B:
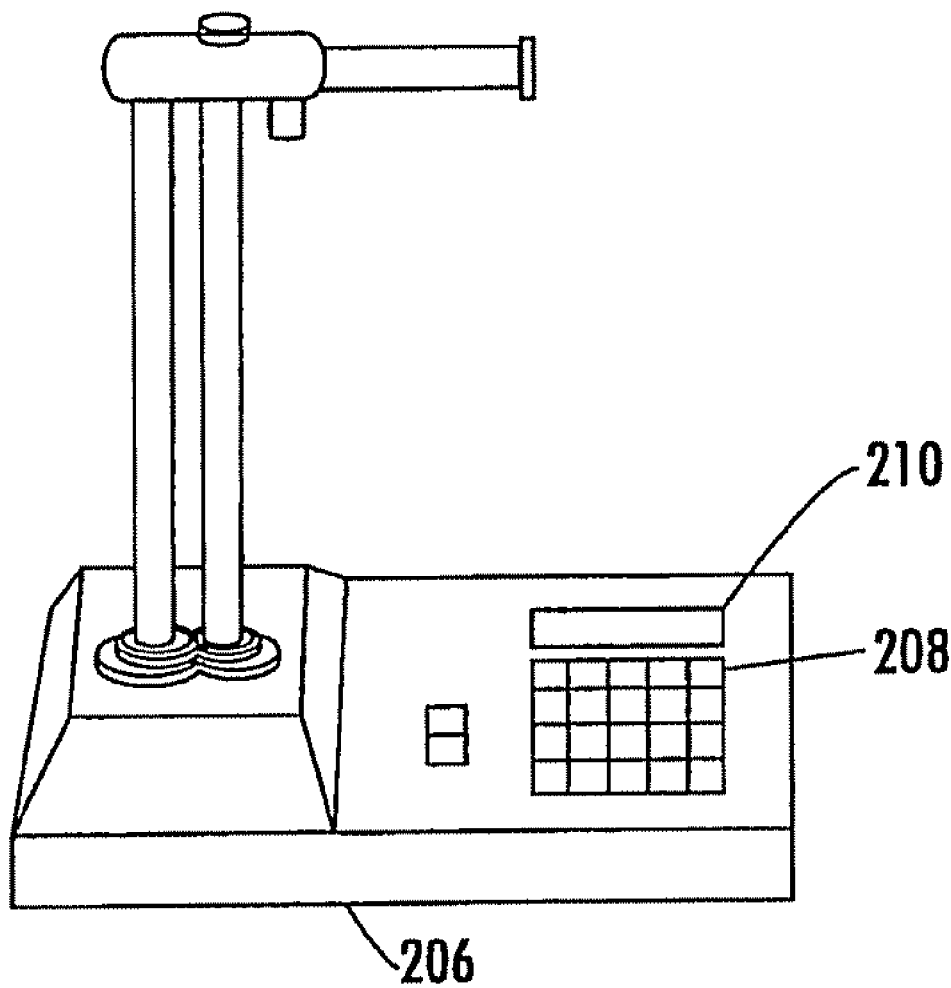
FIG. 2B is a schematic view showing more detail of a measuring/locating/tracking device according to an embodiment of the subject matter described herein.

In one embodiment the functionality of computer device 202 may be entirely or at least partially contained within measuring/locating/tracking device 200. FIG. 2B is a schematic view of an exemplary self-contained measuring/locating/tracking device 206 according to an embodiment of the subject matter described herein. For example, device 206 can include the function of devices 200 and 202 shown in FIG. 2A. In particular, device 206 can include location functionality, such as GPS, as described herein. Further, device 206 can include a keypad 208 and an LCD display 210 for user interface.

Figure 3:
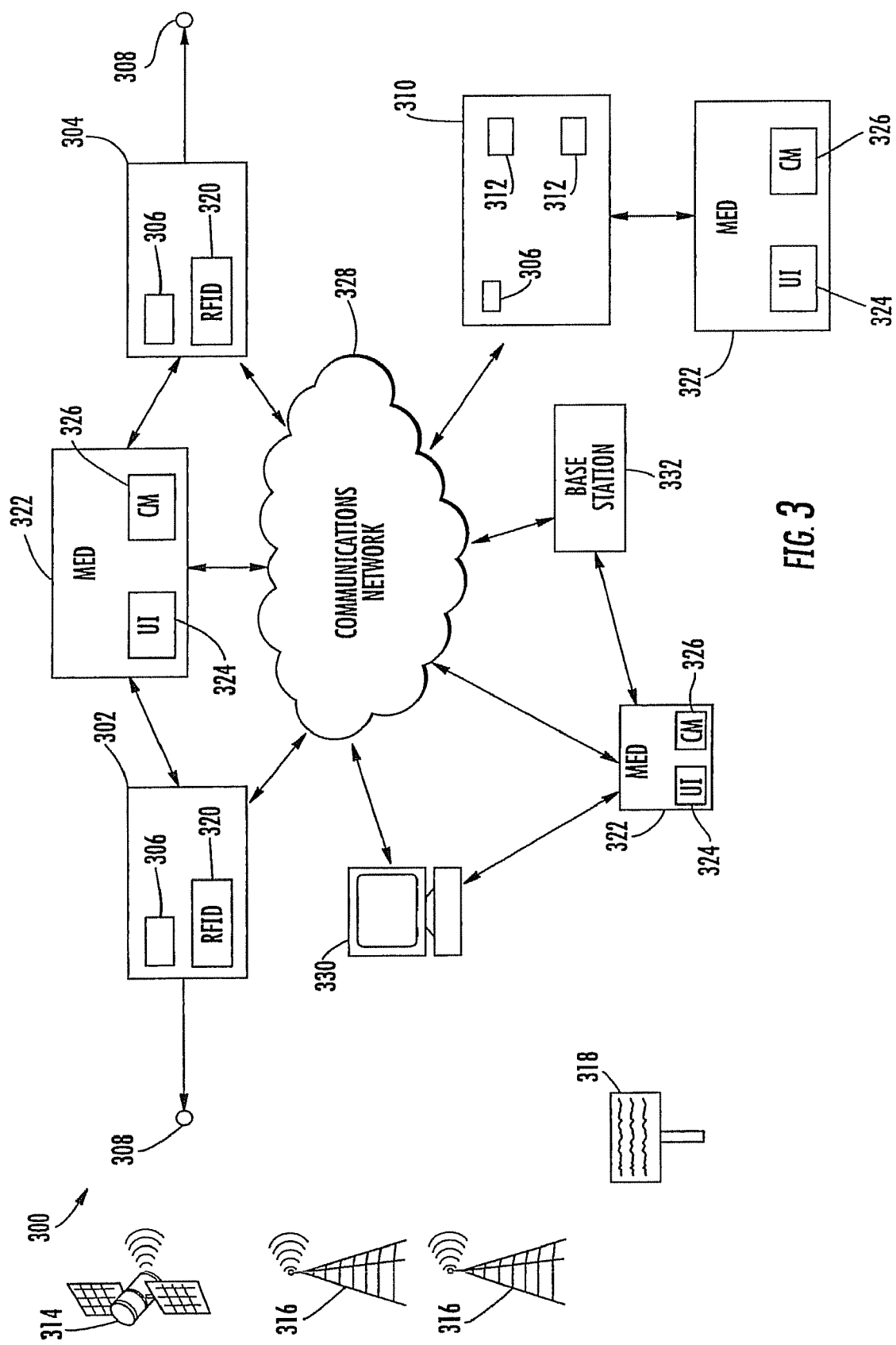
FIG. 3 is a schematic view of an exemplary system for locating and tracking measuring devices and identifying the locations to one or more mobile electronic devices remote from the measuring devices according to an embodiment of the subject matter described herein.

FIG. 3 illustrates a schematic, view of an exemplary system 300 for locating and tracking measuring devices and identifying the locations to one or more electronic devices remote from the measuring devices according to an embodiment of the subject matter described herein. Referring to FIG. 3, system 300 may include measuring devices 302 and 304 and corresponding tracking systems 306. Measuring devices 302 and 304 can be configured to measure one or more properties of samples 308. Exemplary properties that can be measured include density, porosity, void content, moisture content, modulus, permeability, permittivity, strength, stiffness and/or soil classification. In this example, a corresponding tracking system 306 can be integrated into the same unit as measuring devices 302 and 304. Alternatively, tracking systems may be contained in separate units than measuring devices. System 300 may also include a shipping container 310 adapted to carry cargo such as measuring devices 312. Measuring devices 312 may also represent location services attached to hazardous materials or cargo in addition to measuring devices. Shipping container 310 may include tracking system 306 for determining a position/location of measuring devices 312 during transport in container 310. Alternatively, measuring devices 312 may each include a tracking system for determining a position/location. Shipping container 310 may be re-positioned by vehicles such as a ship, automobile, airplane, train, truck or other suitable vehicle for transporting a shipping container.

A shipping container can be described as an individual shipping case or a large container suitable for transporting several tons of products or devices. A large container can be a container suitable for transporting goods by sea, air, and/or ground. Typically these containers are metal and sealed from the weather, so radio communications to the interior of such a container is generally impossible. In one example, an individual shipping case can be used for transporting nuclear instrumentation, such as a nuclear gauge. Some authorities require that carrying cases for transporting nuclear sources or instrumentation be securely locked and fastened in place during transportation. It would be of interest to configure this case with an alarm system for notifying authorities when an unauthorized entry into the case is detected. Such an alarm system can be configured according to the subject matter described herein for communicating alarm information to a remote device operated or monitored by a proper authority.

Tracking systems 306 may be configured to determine a position/location of a device. For example, tracking system 306 corresponding to measuring device 302 may be configured to determine the coordinates of a position/location of measuring device 302 at a position/location of a sample measurement. In one embodiment, tracking systems 306 may be configured to receive satellite positioning information, such as GPS information, from one or more positioning satellites 314 for determining a position/location of measuring device 302. In another embodiment, multiple mobile communications towers 316 (e.g., cell phone towers) can transmit radio waves to tracking system 306, which can be adapted to receive the information and to determine or enhance a position/location based on the triangulation of the received waves. One example is AFLT or Advanced Forward Link Trilateration. Another example incorporates the GPSONE® technology available from QUALCOMM Incorporated, of San Diego, Calif. In another embodiment, tracking systems 306 may be configured to receive position/location information from a signpost beacon 318 and to determine a position/location based on the information. Tracking system 306 may also include an RFID tag 320 for identifying measuring device 302 with a position/location/identification of measuring device 302. RFID tag 320 may be integrated into a measuring device or separate from a measuring device. The RFID may be associated with location services or be enabled as a stand-alone identification or authorization module.

System 300 may include mobile communications devices 322 that comprise a user interface 324 and a communications module 326. Exemplary communications devices include a mobile telephone, a smart device, a cell phone, a computer, a PDA, or any other suitable communications device. User interface 324 can receive input from a user and present output information to a user, such as with a display and/or a speaker. Communications module 326 is configured for communicating with other devices. For example, communications module 326 may be configured for wireless and/or wired communication with devices via a direct and/or indirect connection. Device 322 can, for example, be used for transmitting and receiving programs, updates, data and the like. The device can also communicate to other mobile devices through network 328.

System 300 may include a communications network 328 configured to exchange information and data between network-enabled devices. Measuring devices 302, 304, and 312, and/or shipping container 310 can be network-enabled for exchanging information and data via communications network 328. For example, measuring devices 302, 304, and 312, and/or shipping container 310 can exchange position/location/identification-related information and/or sample measurement information via communications network 328. Mobile electronic device 322 can be network-enabled for receiving position/location-related information and/or sample measurement information from measuring devices 302, 304, and 312, and/or shipping container 310 via communications network 328. Communications network 328 can include one or more different communications networks adapted for exchanging information and data between one another. Exemplary communications networks include the Internet, the PSTN, an analog network, a digital network, a cellular network, and/or any other suitable communications network. Measuring devices 302, 304, and 312, and/or shipping container 310 can be configured to communicate position/location-related information and/or sample measurement information to mobile electronic device 322, a central computer system 330, a base station 332, and/or any other network component via communications network 328. The position/location-related information and/or sample measurement information can be communicated to device 322 via central computer system 330 or base station 332. Device 322 may also communicate information to a measuring device via network 328. The communicated information can include information for positioning a measuring device for sample measurements or for polling the measuring device for position/location-related information and/or identity information. In one embodiment, devices 322 may communicate directly with devices 302, 304, and 312, and/or shipping container 310. Measuring devices 302, 304, and 312 may be a nuclear density gauge, or a homeland security dosimeter equipped with an RFID reader. In one example, measuring device 302 may be a homeland security device equipped to identify the elements or characteristics of device 304. Here, network 328 may utilize the RFIID communications protocol. Location devices 306 may or may not be included in this example.

In one example, devices 302 or 304 may represent a quality control gauge (e.g. a gauge available from Troxler Electronic Laboratories, Inc.) equipped with an RFID tag. The tag may be coded with relevant information that could be encrypted. Upon receiving an excitation from a RFID reader, spectrum information could be transmitted and matched with actual measurements from the requestor. Other information such as MSDS, ownership and government authorization codes could also be available to the reader in an encrypted format. In another example, device 302 may function as the RFID interrogator operated by an authoritative figure. In this example, device 302 may be used to evaluate cargo or field equipment 304 equipped with an RF tag containing information to communicate via device 328.

In one embodiment, measuring devices 302, 304, and 312, and/or shipping container 310 can directly communicate position/location-related information and/or sample measurement information to device 322. In this embodiment, communication of the information can be completed without the use of network 328. For example, the information can be directly communicated from one of measuring devices 302, 304, and 312, and shipping container 310 to system 330, which can forward the information to device 322 by use of communication network 328 or any other suitable communication technique. Device 322 may also directly communicate information to a measuring device for positioning a measuring device for sample measurements or for polling the measuring device for position/location-related information and/or identity information.

In one example, communications network 328 can be a mobile communications network. In this example, measuring devices 302, 304, and 312, and/or shipping container 310 can communicate position/location-related information and/or sample measurement information to one of communications towers 316. Towers 316 can be configured to forward the information to device 322 via the mobile communications network. Device 322 may also communicate information to a measuring device via the mobile communications network. Satellite communications may be utilized. The communicated information can include information for positioning a measuring device for sample measurements or for polling the measuring device for position/location-related information and/or identity information.

Figure 4:
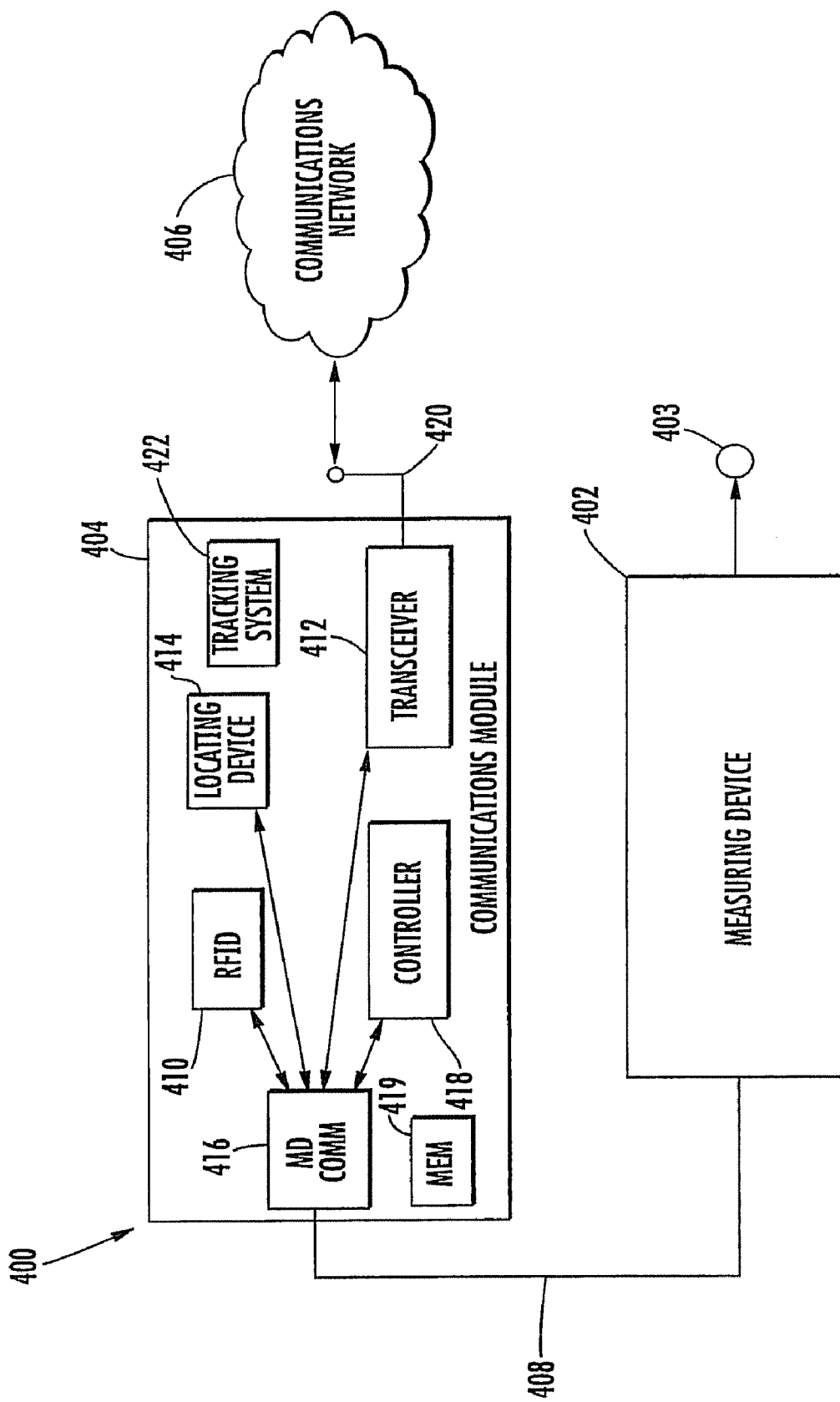
FIG. 4 is a block diagram of an exemplary measuring/locating/tracking system according to an embodiment of the subject matter described herein.

FIG. 4 illustrates a block diagram of an exemplary measuring/locating/tracking/identifying system 400 according to an embodiment of the subject matter described herein. Referring to FIG. 4, system 400 can include a measuring device 402 configured to measure one or more properties or characteristics of a material or sample 403. System 400 can also include a communications module 404 configured to communicate with network-enabled devices via a communications network 406. Communications module 404 and measuring device 402 can communicate via a communication element 408 (shown in this example as a wire, or a trace on a PC board).

Communications module 404 can include combinations of an RFID module 410, a transceiver 412, a locating device 414, a measuring device communications function 416, a controller 418, and a memory 419. RFID module 410 can be configured to store identification information for device 402 and module 404. Further, RFID module 410 can store identification information for electronically keying device 402 with module 404. RFID module 410 can also store or communicate inventory information, hazardous material database, expected hazardous material spectrums or characteristics, MSDS information routing information, and the like. Communications module 404 can receive a polling signal for identification and/or inventory information from networks other than a typical RFID short range response. In response to receiving a polling signal, the identification, inventory, and/or routing information can be retrieved from RFID module 410 and sent to an originator of the polling signal anywhere on the globe. Transceiver 412 can include an antenna 420 for communicating with communications network 406. A polling signal can be received from a network-enabled device via communications network 406. The response to a polling request may be disabled if the originating signal does not contain the appropriate authenticated identification in order to prevent eavesdropping or tampering with the confidential information that transmits between parties. Various data and programs can be stored in memory 419.

In one embodiment, communications module 404 can be configured in a direct notification system to communicate information with a base station (such as base station 332 shown in FIG. 3). For example, the base station can be a dedicated computer system for receiving from and transmitting to communications module 404 data, programs, and instructions. In another embodiment, communications module 404 can be a mobile telephone, a PDA, a PNA, or another suitable portable communications device configured to communicate information via a mobile telephone network, such as a cellular telephone network. In another embodiment, the communication channel may enable a virtual private network that enables confidential transmission of key information between parties. Communication module 404 may contain all the necessary confidentiality/key protocols and encryption and authentication techniques that are well understood by those knowledgeable in the art. Examples of such protocols and techniques are the Data Encryption Standard from NIST, the Advanced Encryption standard; secure Hash Algorithms, Secure Socket Layers, EI-Gamma Algorithm, Diffie Hellman key exchange, open PGP, digital certificates using a certificate authority, public key secure sockets layer (SSL), transport layer security (TLS), and combinations of public key and symmetry techniques. These techniques could involve block ciphers, stream ciphers or combinations thereof. Examples of authenticating a request include passwords, pass cards, digital signatures, and biometrics, such as fingerprint, retinal scans, face scans, and voice identification and such. In multifactor authorization, there may be multiple tests to secure the transfer of information. For instance, you may have a token, a password, and a biometric identification, such as a fingerprint.

Antenna 420 can be integrated into a body of communications module 404. In one example, antenna 420 can be a microstrip antenna attached on the outside of a casing. In another example, antenna 420 can be a metallic rod functioning as a monopole or dipole. In another example, antenna 420 can be integrated into a body in a stealth manner such that the antenna is hidden from view or difficult to find.

In another embodiment, communications module 404 can be configured in a direct notification system such that a central computer system (such as central computer system 109) can monitor a position/location of measuring device 402 by receiving position/information location from locating device 414. The central computer system can notify third parties of the position/location of measuring device 402 via a communications network such as the Internet, mobile telephone communication, plain old telephone service (POTS), facsimile, and other suitable forms of electronic communication.

The third party notification can include shipping, routing and/or status information of measuring device 402.

Controller 418 can include suitable hardware, software, and/or firmware components for managing the components of module 404. Further, controller 418 can include suitable memory for storing software and identification, inventory, and/or routing information. RFID module 410 can be distributed for use in association with a particular measuring device by a third party. For example, RFID module 410 can include an RFID chip distributed by a government agency for tracking and identifying a nuclear gauge or hazardous material. Measuring device communications function 416 can communicate instructions, data, and/or programs to measuring device 402. Further, controller 418 can control the execution of programs from communications module 404 for sending alarms to a third party. Individual components 410, 414, 420, and 422 can be optionally included in combination or alone.

Locating device 414 can determine a position/location of measuring device 402 and/or communications module 404. A position/location can be determined by any suitable technique such as GPS. In one embodiment, locating device 414 can be configured to determine a position/location of measuring device 402 when or nearly when a sample measurement is acquired. For example, measuring device 402 can indicate to communications module 404 when a sample measurement is acquired. In this example, the sample measurement indication can trigger a determination of a position/location of measuring device 402. If the location is already active, the trigger can result in writing the data to the proper memory location. Communications module 404 can communicate the sample measurement and position/location of measuring device 402 to network-enabled devices in communication with communications network 406. Alternatively, the measurement could be stored on 404 or 402 for retrieval at a later time and place such as at the end of the day or end of the project. Further, the sample measurement and position/location/identification information can be forwarded to a mobile communications tower, a base station, and/or a central computer system.

Communications module 404 can include a tracking system 422 configured to store tracking information associated with measuring device 402. In one embodiment, the tracking information can include identification information for measuring device 402. For example, tracking system 422 can retrieve identification information for measuring device 402 that is stored and shared with RFID module 410. The tracking information stored in tracking system 422 can also include routing information for defining a predetermined route for moving measuring device 402 and/or boundary information for defining a predetermined boundary for measuring device 402. Communications module 404 can communicate a signal to a network-enabled device connected to network 406, a base station, and/or central computer system that includes the tracking information associated with measuring device 402.

Further, communications module 404 can determine whether the position of measuring device 402 is following the predetermined route and/or within the predetermined boundary. For example, communications module 404 can determine whether the distance between the position of measuring device 402 and the predetermined line of route or predetermined boundary is equal to and/or greater than a predetermined distance. In this example, if it is determined that the distance between the position of measuring device 402 and the predetermined route or predetermined boundary is equal to and/or greater than a predetermined distance, communications module 404 can transmit a notification signal or alarm to a network-enabled device connected to network 406, a base station, and/or central computer system. In another example, communications module 404 can determine whether measuring device 402 is within the predetermined boundary. In this example, if it is determined that measuring device 402 is within the predetermined boundary, communications module 404 can notify a network-enabled device connected to network 406, a base station, and/or central computer system of this condition. In general, the boundary proximity system tests for location breaches whereby the object is allowed to be inside a boundary, outside a boundary, inside or outside a corridor or 3D space. Further, communications module 404 can store a record of the positions of measuring device 402 over a period of time and/or the position of measuring device 402 with respect to the predetermined route and/or the predetermined boundary over a period of time. Communications module 404 can communicate the record to a network-enabled device connected to network 406, a base station, and/or central computer system. For example, the record can be communicated to another device when polled or automatically if the proper authorization is verified. The record could also be downloaded later in time.

In one embodiment, communications module 404 can be configured as a stand-alone system in which locating device 414 includes "smart" positioning functionality. For example, locating device 414 can comprise a smart GPS system including communications, alarms, and capabilities for notifying other devices of a position of measuring device 402 with respect to a predetermined boundary and/or predetermined route. In this example, controller 418 can include advanced memory and programming capability for implementing the smart GPS system. An alarm of position information can be communicated via transceiver 412 and antenna 420. Further, the alarm can be communicated to a user of measuring device 402 via a speaker, display, text messaging, Internet, cell phone, physical action, and/or any other suitable technique for notifying a user of a system condition. In one example, locating device 414 can comprise an advanced microprocessor, memory, and/or software for maintaining a plurality of states and determining an alarm state.

In one embodiment, an alarm can be activated for notifying a remote device of a system failure and/or a position alarm. For example, a system failure can occur when one or more functionalities of measuring device 402 and/or communications module 404 fails. In another example, a position alarm can occur when it is determined that measuring device 402 is a predetermined distance from a predetermined route and/or predetermined boundary. An alarm or notification of the system failure or position condition can be communicated to a remote device via a base station, a mobile telephone tower, and/or the Internet. In one example of the case of an alarm condition, communications module 404 can automatically place a mobile telephone call to a designated remote device and provide alarm condition information and a position, such as the last known position, of measuring device 402 and/or communications module 404. Alarms can also be activated when the communications module 404 is tampered with or when the software or boundaries are altered without the proper authorization and authentication protocols and/or keys.

In one embodiment, a system failure can occur when a component of measuring device 402 and/or communications module 404 is tampered with and/or removed. For example, in the case of a nuclear gauge, the nuclear gauge can contain a radioactive source and one or more detectors for determining whether the radioactive source has been tampered with and/or removed. The detectors can perform a radioactivity count for comparison to a predetermined or expected value. If the count is less than the predetermined or expected count value, an alarm can be communicated to a remote device. Other detectors can determine whether a container for holding or storing a component has been opened, such as the opening of a seal of a radioactive source case. In a stand-alone system, components for determining that a component has been tampered with and/or removed can be integrated entirely or at least partially within measuring device 402 and/or communications module 404. In one example, an alarm can be communicated to a remote device in response to detection of a sudden change in the count value detected by a detector. In another example, an alarm can be communicated if a wire such as a security seal is broken.

In another embodiment, communications module 404 can determine diagnostic information and calibration or service information of measuring device 402. Exemplary diagnostic information includes radioactive source strength, battery life, drift tests, high voltage readings, low voltage readings, and other suitable diagnostic information of a measuring device. The diagnostic and calibration information along with the health of the sensors and systems can be communicated to a remote device according to the techniques described herein. For instance, a change in the count rate could be caused from a component slipping, an amplifier or detector failure, or tampering with components. This could result in the alarm state related to the health of the instrument being triggered.

In one embodiment, communications module 404 can be configured in a remote positioning approach wherein a central computer system provides support for determining a state of measuring device 402 and for controlling measuring device 402. The central computer system can maintain regular communication with communications module 404 for determining states and for controlling measuring device 402. For example, the central computer system can communicate polling signals to communications module 404 for determining a position/location of measuring device 402. The position/location/identification of measuring device 402 can be determined by locating device 414 and communicated to the central computer system. The central computer system can use the position/location/identification information to determine whether measuring device 402 is within a predetermined distance of a predetermined route, within a predetermined boundary, and/or within a predetermined distance of a predetermined boundary. The central computer system can store information defining the predetermined route and/or the predetermined boundary. The route and boundary information can be updated and altered by an operator or other suitable control source. The predetermined route and the predetermined boundary can define areas that measuring device 402 is allowed to be transported in and near. For example, the border of Mexico can be a boundary which is defined in the central computer system as coordinates. An alarm can be activated if measuring device 402 is moved across a predetermined boundary and/or a predetermined distance from a predetermined route. For some equipment, it may be desirable to hard code the alarm boundary as it may be seldom or never changed.

There are at least two ways for implementing alarm functionality. One is that the location information is sent to central computer system that performs all calculations, alarms and notifications; the other way is if the entire system is local to the equipment and autonomous. All or a portion of the calculations can be performed onboard. All or a portion of the alarms and notifications can be either stored for later retrieval, or linked when necessary via the onboard electronics. For route monitoring, the designated waypoints can be programmed into communication module 404 before leaving the port, and be self sufficient.

Figure 5:
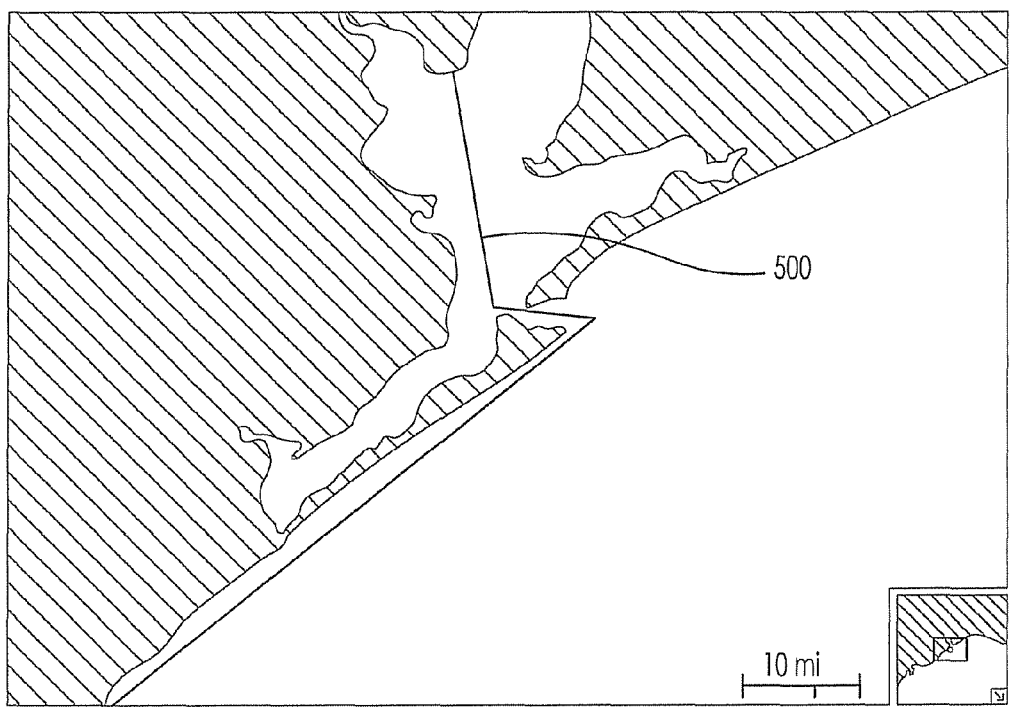
FIG. 5 is a geographic map showing an exemplary planned shipping route for transporting a nuclear gauge or hazardous material.

FIG. 5 illustrates a geographic map showing an exemplary planned shipping route for transporting a nuclear gauge. A predetermined route 500 indicates a predetermined route for transporting a nuclear gauge along the sea near Galveston, Tex. A communications module can store the predetermined route. Further, the communications module can include a locating device for determining the location of the nuclear gauge. Using the stored predetermined route and the location of the nuclear gauge, the communications module can determine whether the nuclear gauge deviates greater than a predetermined distance from the predetermined route. Further, in response to determining that the nuclear gauge deviates greater than the predetermined distance from the predetermined route, the communications module can indicate or alert another device to the condition.

FIG. 6 illustrates a geographic map showing an exemplary boundary for a nuclear gauge. A predetermined boundary 600 indicates a predetermined boundary for a nuclear gauge. A communications module can store the predetermined boundary. Further, the communications module can include a locating device for determining the location of the nuclear gauge. Using the stored predetermined boundary and the location of the nuclear gauge, the communications module can determine whether the nuclear gauge is outside the boundary and/or a predetermined distance from the boundary. Further, in response to determining that the nuclear gauge is outside the boundary and/or a predetermined distance from the boundary, the communications module can indicate or alert another device to the condition. Boundaries can be any shape or size, and be as simple as a radius, or have many complex lines.

In another embodiment, a device that is remote from a measuring device can store a predetermined route and/or predetermined boundary for the measuring device. For example, the remote device can be a network-enabled device connected to network 406, a base station, and/or central computer system configured to receive signals indicating a position of the measuring device. The remote device can compare the position of the measuring device to the stored predetermined route for determining whether the measuring device is a predetermined distance from the predetermined route. Further, the remote device can compare the position of the measuring device to the stored predetermined boundary for determining whether the measuring device is a predetermined distance from the predetermined boundary. The remote device can also determine whether the measuring device is within the predetermined boundary. The remote device can notify another device to the position of the measuring device with respect to the predetermined route and/or predetermined boundary. Further, the remote device can store a record of the position of the measuring device and/or its position with respect to the predetermined route and/or the predetermined boundary.

In one embodiment, a measuring device and/or communications module associated with the measuring device can receive one or more signals that poll for the location of the measuring device and/or communication device. In response to receiving the poll, the communications module can communicate a location of the measuring device. In one example, in the case of the measuring device being stolen, the communicated location can be the last known location of the measuring device. The communications can be via landline, POTS, mobile telephone, radio, or satellite communications. For mobile telephone communications, communications module and/or measuring device can include functionality for communicating via a mobile telephone network. In one example, a measuring device can be associated with a telephone number and account. In another example, a signal associated with a measuring device can comprise a communications channel coded with an identification number or serial number of the measuring device for use in identifying the measuring device. In this example, a single telephone number or communication channel can be shared among a plurality of measuring devices because each measuring device can be identified and information modulated by a unique identification number or serial number coded into a communications channel. A suitable addressing technique, such as a technique used in a "daisy chain" system, a multiplex/de-multiplex system or an address loop system utilized as, for example, the HP general purpose interface bus (GPIB) method can be used for identifying and talking to particular addressed measuring devices.

Another suitable addressing technique may include broadcasting; multicasting protocols such as those used in the Internet Protocol version 4 or 6. One example is RFC 919 from the Internet Engineering Task Force (IETF). An identification system for identifying a measuring device can be advantageous, for example, because measuring devices can respond to polling signals in a party line fashion, and thus reduce the expenses associated with mobile communications services. In an example of its use, a contractor or owner of the measuring device can communicate a poll message by calling a telephone number and inputting a code identifying the measuring device. In this example, the input code can be demodulated and a corresponding measuring device can reply.

Figure 7B:
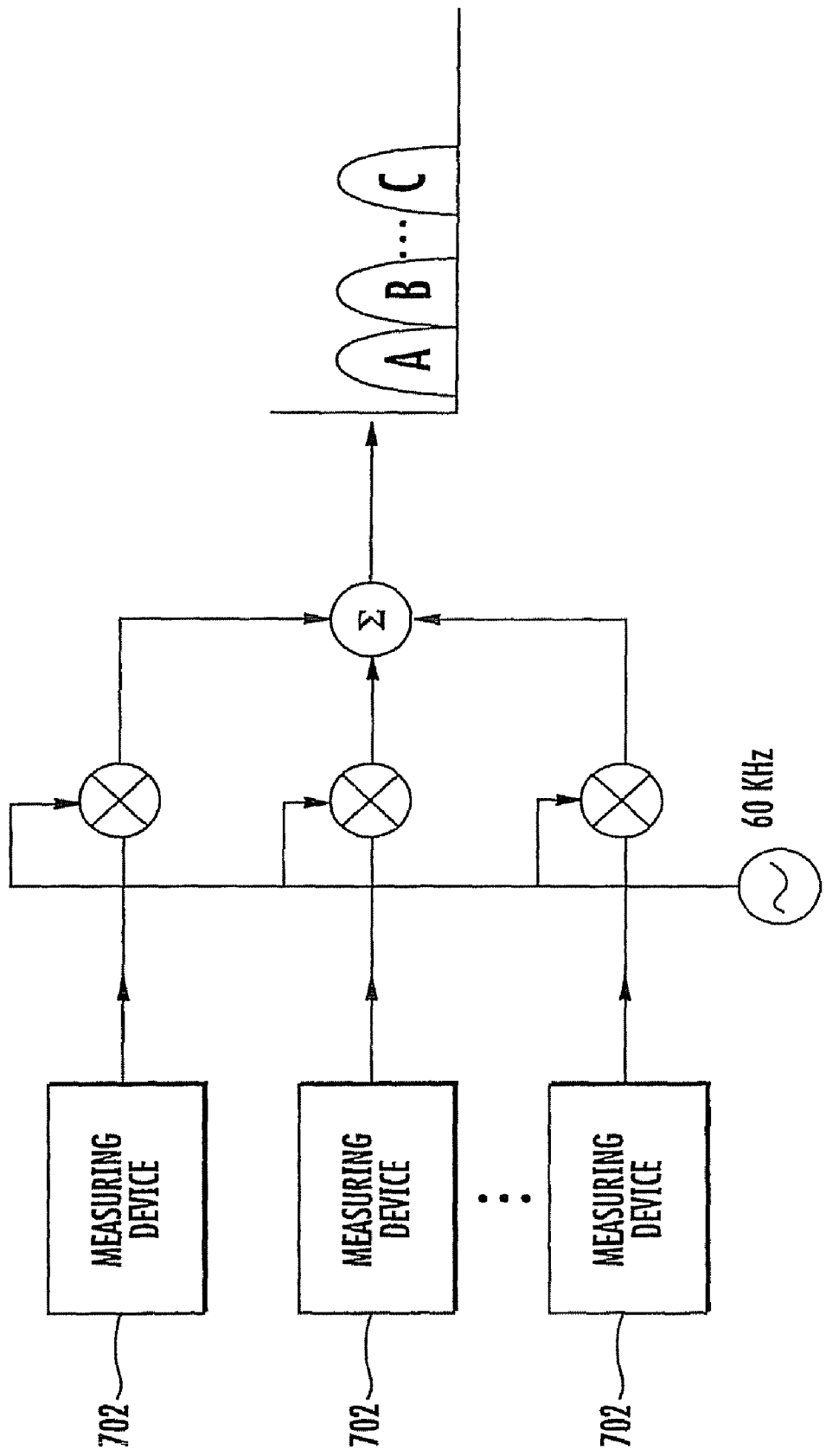

Network channels can be multiplexed and demultiplexed in accordance with the subject matter described herein by any suitable technique. Exemplary multiplexing and demultiplexing techniques include time division multiplexing, frequency division multiplexing, wavelength division multiplexing, and statistical multiplexing. In one example of a statistical multiplexing technique, an orthogonal code-hopping technique can be utilized in a wireless communications system. In this example, a plurality of synchronized communication channels can be transmitted on a single media. FIGS. 7A and 7B illustrate schematic diagrams of exemplary modulating/demodulating systems in accordance with the subject matter described herein. Referring to FIG. 7A, a modulating/demodulating system 700 includes a plurality of measuring devices 702 and corresponding communications modules 704 are configured to share a common communications channel 706. Communications channel can be mobile telephone communications channel or any other suitable communications channel that can be shared among a plurality of devices for communication. Communications modules 704 can each include an encoder/decoder 708 configured to encode and decode communications on channel 706. Further, communications modules can be configured to utilize wireless multiplexing and demultiplexing techniques such as daisy chain looping, HPIB, or any other suitable technique. Each measuring device 702 can be associated with identification information, such as a serial number or name. The identification information can be encrypted into its corresponding address/data bus 710.

FIG. 7B shows a diagram of providing a frequency offset for each measuring device 702 in communications on channel 706. The frequency offset for each measuring device 702 can be a function of its identification information.

Measuring device 702 can include a GPS system and include the ability to be monitored at a workplace environment, a warehouse, and/or factory. For example, measuring device 702 can be monitored constantly, at intervals, or randomly. Communications can be via mobile telephone technology, POTS, satellite and/or any other suitable technique. In one embodiment, measuring devices detecting or including a gas, solid, liquid, or radioactive material can be remotely monitored. Exemplary monitoring types include inventory monitoring, diagnostic monitoring, a personal dosimeter, environmental conditions such as humidity, temperature and pressure, and device health monitoring. In one example, device health monitoring can include checking a chemical content or location of the measuring device. In one embodiment, a measuring device can be remotely monitored for an actual measurement. In this embodiment, a measurement by the measuring device can trigger the acquisition or recording of location information, which can be stored in a memory of the measuring device or communicated to another device. Further, an operator of a measuring device can initiate measurement and location acquisition.

Measurement and location information can be directly uploaded to a central computer system, a base station, and/or mobile device for storage and analysis. A central computer system, a base station, and/or mobile device can query the condition of a measuring device on demand by an operator or automatically. Automatic querying can be random or periodic at any predetermined interval. Alternatively, the measuring device can communicate measurement and location information autonomously. In one example, a predetermined event can trigger the communication of measurement and location information.

Figure 8A:
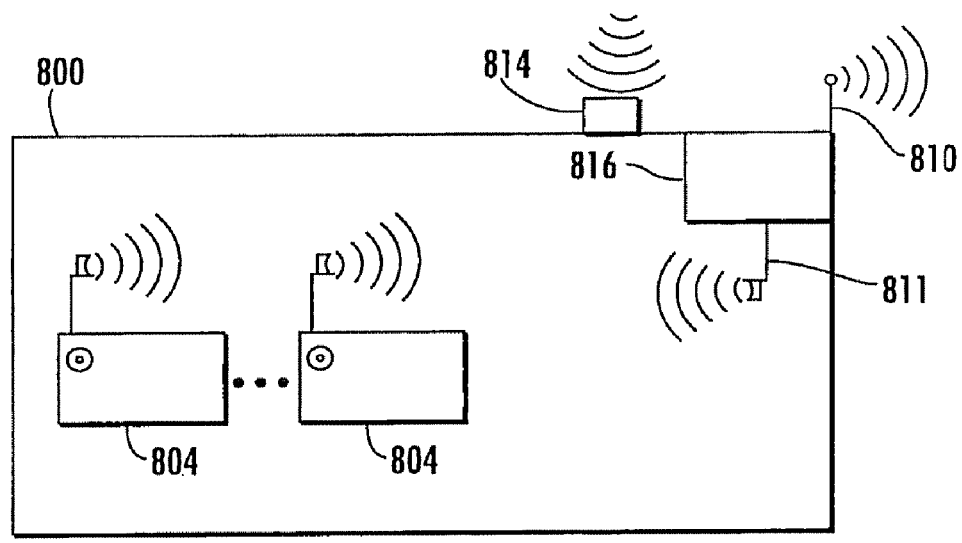
FIGS. 8A and 8B are schematic diagrams of an exemplary container and an exemplary relay system, respectively, for relaying measurement, identification, and/or location information associated with measuring devices according to an embodiment of the subject matter described herein.
Figure 8B:
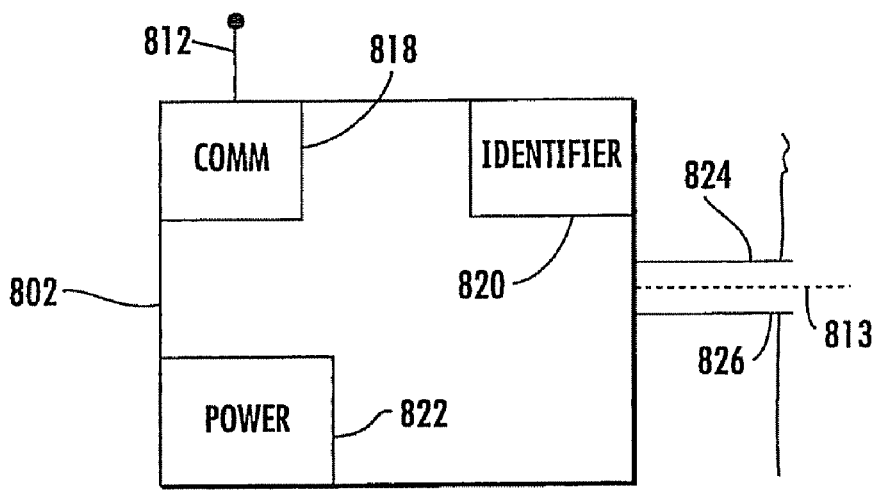

In one embodiment, since the shipping containers are usually metallic and radio signals do not penetrate the shell, a relay module can be configured to relay measurement and/or location information associated with measuring devices. FIGS. 8A and 8B illustrate schematic diagrams of an exemplary container 800 and exemplary relay systems 802 and 816, respectively, for relaying measurement and/or location information associated with measuring devices according to an embodiment of the subject matter described herein. Referring to FIG. 8A, container 800 includes relay system 816. Further, container 800 is holding or storing a plurality of measuring devices 804. Relay system 802 and measuring devices 804 are configured to communicate with one another. For example, relay system 802 and measuring devices 804 can include antennas and corresponding electronics for wireless communication relaying the interior to the exterior of the container. In one example, relay system 802 may be implemented by a re-radiating GPS system having an external antenna that passes a signal inside to an amplifier, where the signal is re-radiated to internal GPS receivers.

Container 800 can include an external antenna 810, an internal antenna 811, an external GPS antenna 814, and a relay device 816 for relaying communications measuring devices 804 and devices external to container 800. The communication channel from the container to the ships bridge could be optical, wireless, or wired with coax for example. Through proper communication techniques, this information can be transmitted off the ship or dock. Measuring devices 804 can emit a unique radio identifier signal in response to being polled by a central computer system or other remote device. The identifier signal and other information can be received by relay device 816 and relayed to an outside device via external antenna 810 or coax. Polling signals can be received by external antenna 810 and relayed to an appropriate measuring device 804 via internal antenna 811. External communications can be implemented by satellite, telephone, mobile telephone, radio, and other suitable communications systems. In this system, the GPS link can be outside of the container, and records the location of the container instead of the object inside. Security information can be passed from the outside to the inside of the container through 810, where it could communicate with the object 804 verifying the object status. Here the object communicates with the outside world via 810 and uses the location of the external GPS 814.

FIG. 8B illustrates more detail of the internal components of relay system 816. Referring to FIG. 8B, relay system 816 can include a communications module 818, an identifier function 820, and a power supply 822. Communications module 818 is configured to manage communications involving antennas 812 and 813. Relay system 802 can include a coax cable 824 and a sealed grommet 826 for external communications. Further, relay system 802 can include an identifier function comprising an encrypted RFID for storing identification information associated with relay system 816 or 802.

In some applications, GPS can be supplemented by other systems when in environments subject to increased signal degradation and obstructions. Measuring device location determinations can be made by using combinations of one or more of GPS, GLONASS, Galileo, or Loran, and GPS-assisted systems such as used in cellular technology. In one example, triangulation techniques can be used with base stations. In another example, a combination of GPS and cellular techniques can result in fast starts of GPS data acquisition. In another example, network assisted GPS involving several technologies may be incorporated. In another example, a combination of GPS and GLONASS can be used for improving the availability and accuracy of satellite signals. Elevation and direction can also be obtained.

Figure 9:
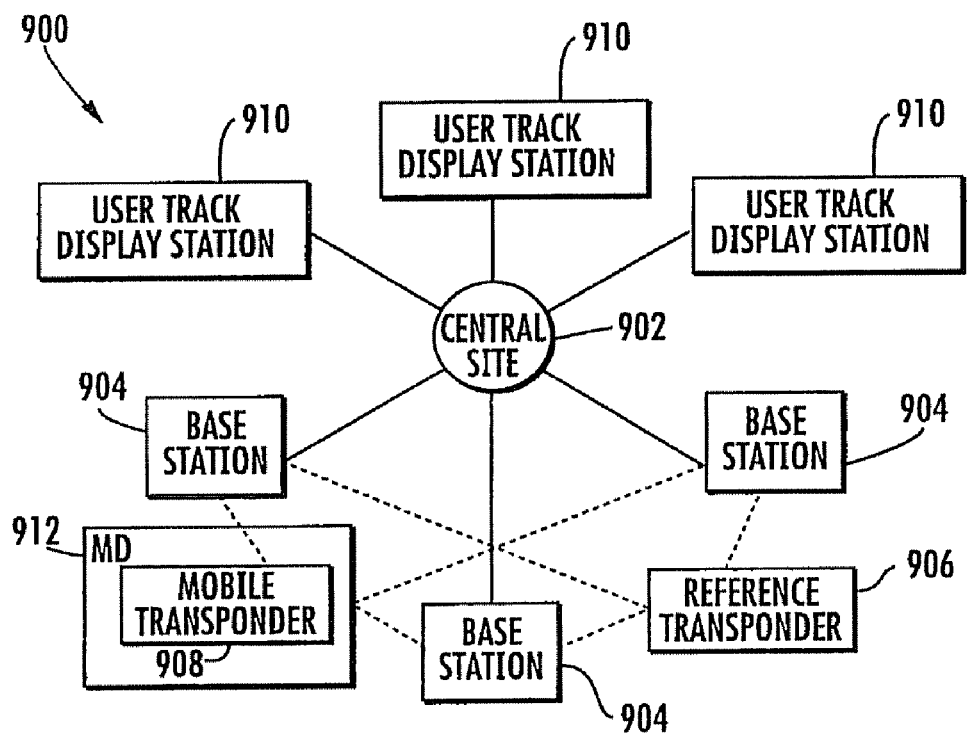
FIG. 9 is a schematic diagram of a terrestrial-based system for locating or enhancing a measuring device according to an embodiment of the subject matter described herein.

A terrestrial-based system can be used for locating a measuring device or another object. FIG. 9 illustrates a schematic diagram of a terrestrial-based system 900 for locating a measuring device according to an embodiment of the subject matter described herein. Referring to FIG. 9, system 900 is based on the QUIKTRAK™ locating system provided by Quiktrak Networks Ltd. of Artarmon, NSW, Australia. System 900 can include a central site 902, a plurality of base stations 904, a reference transponder 906, and a mobile transponder 908. Display stations 910 can make positioning requests to central site 902 to locate a person, place, or object. Central site 902 can send a paging request to a particular transponder 908 to be located. In response, transponder 908 can send a spread spectrum signal that can be received by base stations 904. A time domain analysis technique can be used for determining a position of transponder 908. The position can be sent to the requesting display station 910. A transponder 908 can be positioned near or integrated into a measuring device 912 or another object for determining its location. Although techniques are described herein by which RFID hold encryption or keys, any other suitable techniques may be utilized.

Another exemplary locating system is the mapping systems available from Tele Atlas Data Gent, of Gent, Belgium. These mapping systems can use GPS, a fluxgate compass, an inclinometer, map storage, sensors, and a navigation computer for determining a location of a measuring device. Further, these components can be used for updating and monitoring a position of a measuring device.

Figure 10:
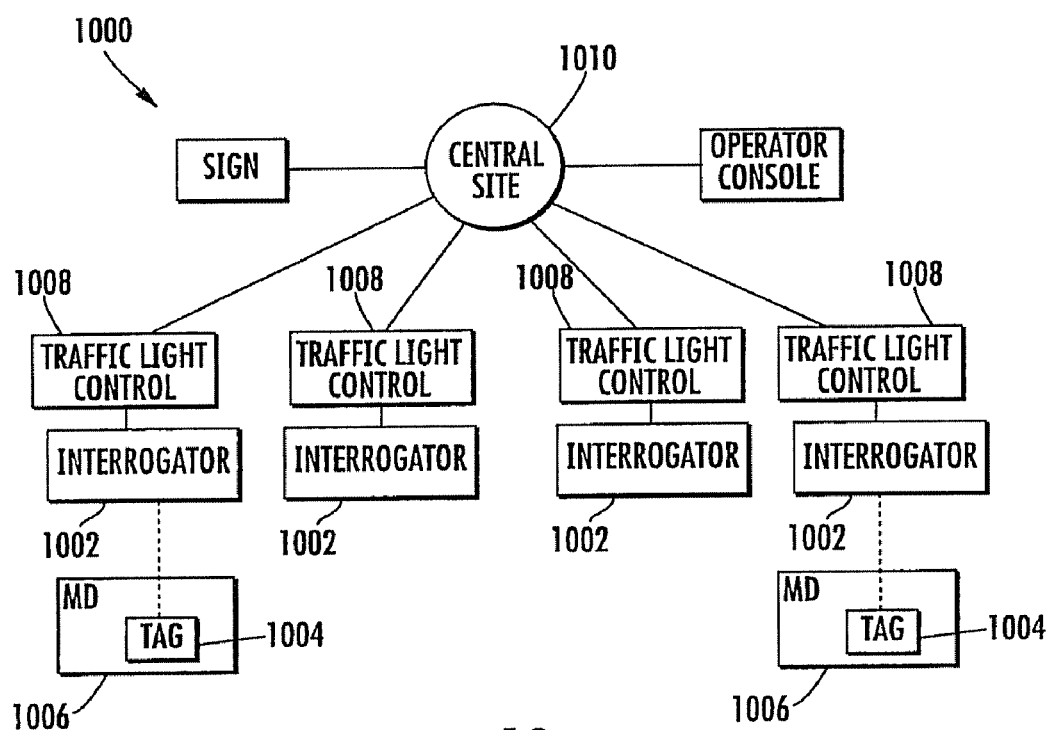
FIG. 10 is a block diagram of an automatic network travel time system or ANUS-based system for locating a measuring device according to the subject matter described herein.

An exemplary signpost-based system for locating a measuring device is the automatic network travel time system (ANUS). ANTIS can use RF tags and interrogators. FIG. 10 illustrates a block diagram of an ANUS-based system 1000 for locating a measuring device according to the subject matter described herein. System 1000 can include a plurality of interrogators 1002 and RF tags 1004. In one example, interrogators 1002 can be mounted or positioned along predetermined locations of highways for use in determining a position of RF tags 1004 that are moved along the highways. Each RF tag 1004 can be attached to, integrated into, or otherwise positioned near a corresponding measuring device 1006 or another object such that the location of a RF tag corresponds to the location of its corresponding measuring device or object.

Interrogators 1002 can include a transmitter and a receiver for communicating with RF signals in the VHF range or any other suitable ranges. Communication power is between about 100 microwatts and about 10 milliwatts. This low power maintains interrogator signaling to areas immediate to the interrogator. Each interrogator 1002 can periodically communicate a tag activation code word comprising framing bits, synchronization bits, and an identifier associated with the interrogator. RF tags 1004 can receive communications from nearby interrogators 1002 and respond with an acknowledgement tag activation code in a handshaking manner.

In one exemplary use of system 1000, each interrogator 1002 can be associated with or attached to a corresponding traffic light control system 1008 positioned at a highway intersection. Measuring device 1006 can be moved towards a highway intersection having an interrogator. As RF tag 1004 associated with measuring device 1006 approaches the intersection, the location of RF tag 1004 can be recorded and forwarded to a central computer system 1010 along with identification information for the measuring device associated with the RF tag. The communications can be integrated with existing communications infrastructure associated with traffic light control system 1008 in order to reduce costs. A hazardous material sensor, such as a radiation monitor or analyzer, can be incorporated into system 1000 for tracking of hazardous material transport. Sensors at the light control box 1008 can activate alarms to central 1010 when a hazardous material was detected.

Figure 11:
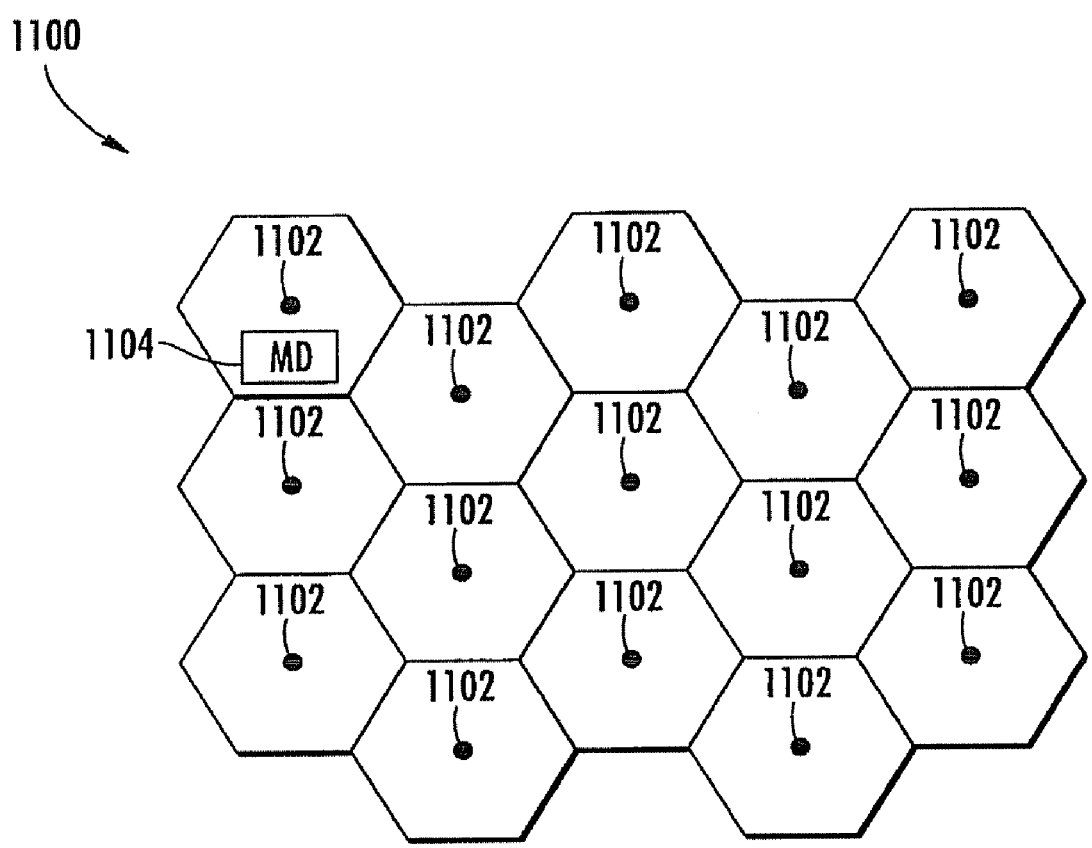
FIG. 11 is a block diagram of a cellular-based communications system for locating or enhancing a measuring device according to the subject matter described herein.

Another exemplary system for locating a measuring device is a cellular-based communications system. A cellular-based communications system can be used for tracking measuring devices and providing boundary alarms. These systems can be the cellular-based systems utilized for communicating with mobile telephones. FIG. 11 illustrates a block diagram of a cellular-based communications system 1100 for locating a measuring device according to the subject matter described herein. Referring to FIG. 11, system 1100 can include a plurality of cell base stations 1102 positioned in a hexagonal cell pattern or any other suitable configuration. A measuring device 1104 having an integrated locating device can move among base stations 1102. Further, measuring device 1104 can be configured with a communications module for communicating with base stations 1102. The communications module of measuring device 1104 can require low power for communication. Further, the communication module can communicate with the base station and be associated with the area in which the measuring device resides. The coverage area of each base station 1102 can depend on its particular location. In rural areas, for example, the coverage area radius can be 30 km. In urban areas, for example, the coverage area radius can be less than 1 km.

Cellular-based communications system 1100 can be used in combination with a satellite-based locating system, such as GPS, for determining a location of measuring device 1104. Systems 1100 can be used to enhance GPS-based systems in cold start ups and when a GPS is receiving poor satellite signals. System 1100 can determine a location of measuring device 1104 based on communications signal strength associated with measuring device 1104, a signal arrival angle, phase measurements of a signal, and/or timing measurements. These measurements can be used in combination with GPS signaling and other location-related information described herein for determining a location of measuring device 1104. Further, the determined location information can be forwarded to a central computer system for analysis and reporting.

Figure 12:
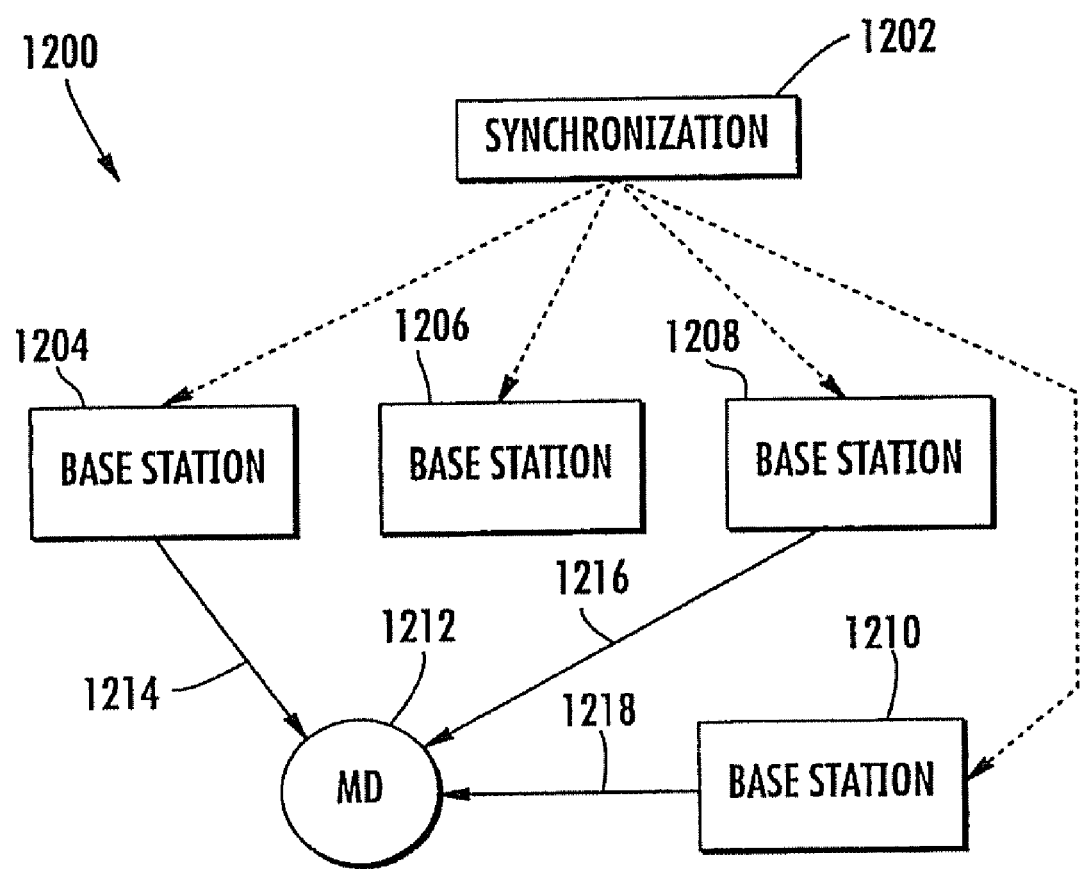
FIG. 12 is a block diagram of an exemplary GSM-based communications system for locating or enhancing a measuring device using a self-positioning technique according to the subject matter described herein.
Figure 13:
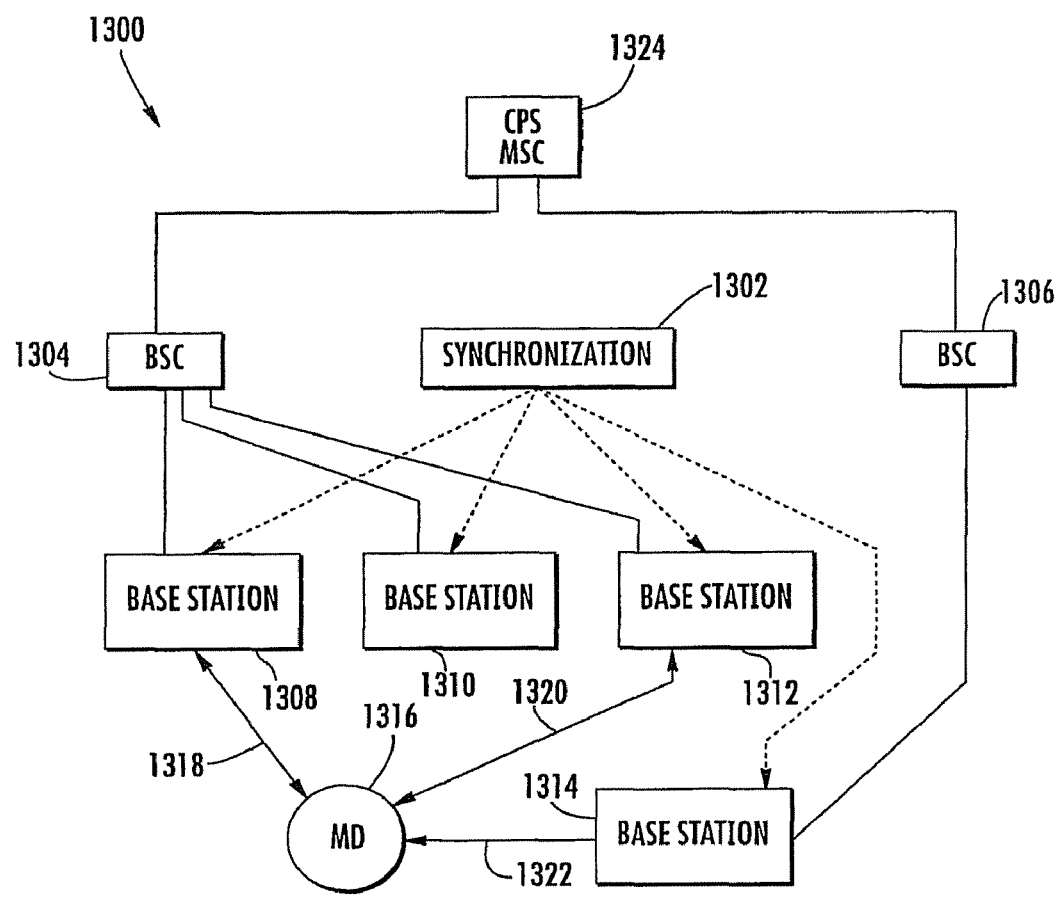
FIG. 13 is a block diagram of an exemplary GSM-based communications system for locating or enhancing a measuring device using a remote positioning technique according to the subject matter described herein.

GSM systems can be used for determining a location of a measuring device. Self-positioning and remote position techniques can be utilized in a GSM system for determining a location of a measuring device. In self-positioning, a measuring device can receive GSM signals from a nearby base station and determine a location based on the signals. FIGS. 12 and 13 illustrate block diagrams of exemplary GSM-based communications systems 1200 and 1300, respectively, for locating a measuring device using self-positioning and remote positioning techniques, according to the subject matter described herein. Referring to FIG. 12, system 1200 includes a synchronization function 1202 and a plurality of base stations 1204, 1206, 1208, and 1210. Synchronization function 1202 can synchronize the operations of base stations 1204, 1206, 1208, and 1210 for providing GSM signaling to a measuring device 1212. Measuring device 1212 can include a communications module for receiving GSM signals from one or more base stations. Further, measuring device 1212 can include a locating device configured to receive GSM signaling from one or more base stations and determine a location based on the GSM signaling. For example, measuring device 1212 can receive signals 1214, 1216, and 1218 from base stations 1204, 1208, and 1210, respectively. The locating device associated with measuring device 1212 can determine a location/position based on GSM signals 1214, 1216, and 1218.

Referring to FIG. 13, system 1300 includes a synchronization function 1302, base station controllers 1304 and 1306, and base stations 1308, 1310, 1312, and 1314. Synchronization function 1302 can synchronize the operations of base stations 1308, 1310, 1312, and 1314 for providing GSM signaling to a measuring device 1316. One or more base stations can receive GSM signals from measuring device 1316. The received GSM signals can be used by system 1300 for determining a location of measuring device 1316. Measuring device 1316 can communicate GSM signals 1318, 1320, and 1322 with base stations 1308, 1312, and 1314. In one example, base stations 1308, 1312, and 1314 can receive GSM signals 1318, 1320, and 1322 communicated from a communications module of measuring device 1316. In this example, information in the received GSM signals 1318, 1320, and 1322 can be forwarded to a mobile switching center (MSC) 1324 via base station controllers 1304 and 1306. MSC 1324 can include a central computer system configured to determine a location of measuring device 1316 based on the information in the received GSM signals 1318, 1320, and 1322.

Systems 1200 and 1300 can include predetermined coordinates that define one or more boundaries and/or one or more routes associated with a measuring device. A boundary can be used to define a geographic area that a measuring device should be positioned within. A route can be used to define a path in a geographic area for moving a measuring device. The measuring device can be associated with a communications module for communicating a position/location of the measuring device and its position/location with respect to the boundary and/or route as described herein. A boundary and/or route can be redefined by an operator. The predetermined coordinates of a boundary or route can be uploaded from a measuring device or a central computer system by using proper user identification information. FIGS. 9-13 illustrate examples of location service possibilities that may be used with GPS for enhanced GPS location services. They may be used alone with reduced accuracy compared to the satellite location techniques.

In one embodiment, actual coordinates of a measuring device may not be determinable. In this event, position vector information can be used to indicate that a measuring device is following a predetermined route or boundary. If actual coordinates are not determined within a predetermined time period, an alarm can be activated. If it is determined that progress is being made to move along a predetermined route, the predetermined time period can be extended. For example, 3D velocity and acceleration vectors can be used to predict future locations of a measuring device or object. In one example, if a ship including monitored cargo deviates from a predetermined route due to a storm, the location, 3D velocity vector, and/or acceleration vector of the ship can be monitored to determine whether the ship is making progress towards its destination. Inertial or optical gyroscopes and magnetic sensors can also improve or augment the system calculations. For stand-alone systems, an authorized operator can input information for ignoring an alarm or contact a remote device.

Figure 14A:
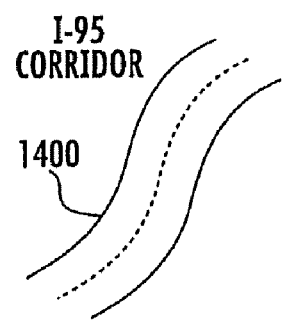
FIGS. 14A and 14B are geographic maps showing an exemplary trucking route and an exemplary shipping/trucking route, respectively, for transporting measuring devices according to embodiments of the subject matter described herein.
Figure 14B:
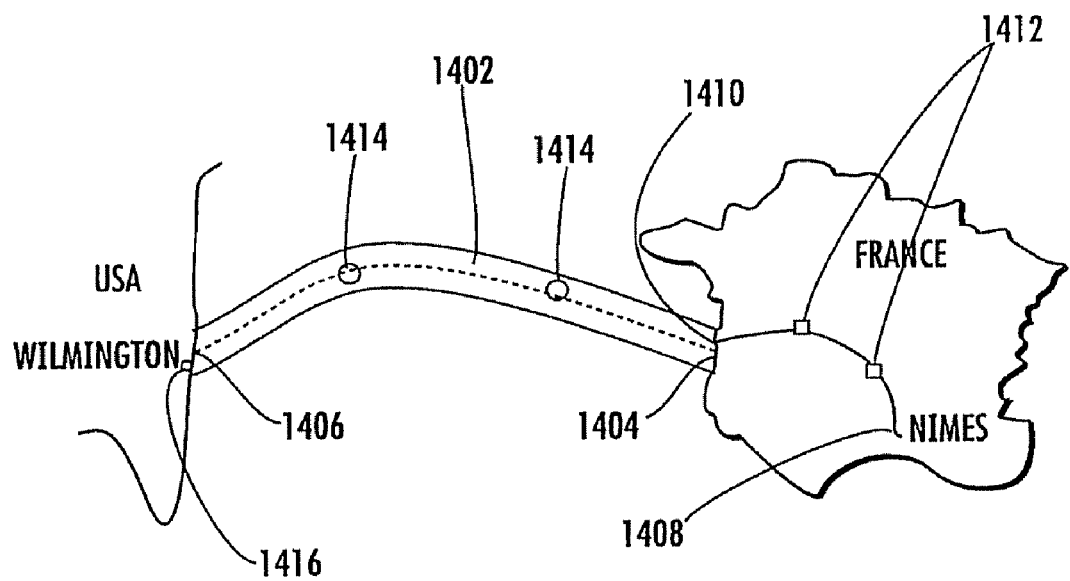

FIGS. 14A and 14B illustrate geographic maps showing an exemplary trucking route and an exemplary shipping/trucking route, respectively, for transporting measuring devices according to embodiments of the subject matter described herein. Referring to FIG. 14A, a highway corridor 1400 is shown for transporting a measuring device. The corridor can be defined by a plurality of predetermined coordinates. A position and/or series of positions of a measuring device can be compared to the predetermined coordinates to determine whether the measuring device is making progress along the highway. Further, the position(s) of the measuring device can be compared to the predetermined coordinates to determine whether the measuring device has deviated a predetermined distance from the highway. If it is determined that the measuring device has deviated greater than the predetermined distance, an alarm can be activated and a signal communicated to a remote device according to the techniques described herein.

Referring to FIG. 14B, a shipping/trucking route 1402 is shown for shipping and trucking a measuring device between France 1404 and North Carolina 1406. A first leg in route 1402 can include trucking a measuring device between an interior city 1408 to a port city 1410 of France 1404. The first leg can include a plurality of trucking checkpoints 1412. A second leg in route 1402 can include a plurality of sea checkpoints 1414. The end of route 1402 can include an end checkpoint 1416. The measuring device can include a locating device for determining its position. Further, the measuring device can include functionality for determining whether the measuring device is located at checkpoints within a predetermined period of time. If the measuring device does not arrive at a checkpoint within the predetermined period of time and/or the measuring device deviates from route 1402, a remote device can be notified. In one example, checkpoints may be coordinate readings, whereby the system decides the proper action from a list of "no action", "alarm", or even "storage" of the points of note.

In one embodiment, a predetermined boundary or route can be changed. For example, new coordinates can be downloaded to a measuring device from an authorized remote device via the communications techniques described herein.

In one embodiment, a measuring device can include embedded programs that can be activated by parameters remotely downloaded for tracking, operational, or transferring data. In one example, calibration constants can be stored in a measuring device when a proper encrypted code is obtained from a remote device. This feature can be advantageous, for example, for preventing unqualified technicians from servicing the measuring device.

In one embodiment, the operation of a measuring device can be controlled by a remote device over any suitable communications technique. For example, control commands can be communicated to a measuring device via the Internet. In another example, control commands can be communicated to a measuring device via a base station PDA or mobile telephone. The commands can result from a measuring device status determination occurring at the remote device.

In another embodiment, alarms can be automatically generated by a remote device as a result of a status or health of a measuring device and/or a location of the measuring device with respect to predetermined boundaries and/or routes. In one example, control programs can obtain a measurement and alert authorities at a remote location with the measurement status, health, and/or location of a measuring device. In this example, the information can be displayed to authorized personnel. The status information can be automatically sent to a central computer system, or when devices are polled. In the event that the measuring device fails to reply to polling, a last known location and status can be incorporated by the central computer system. Exemplary information sent in an alarm signal can include hazardous material identification and MSDS information. Further, the information sent in an alarm signal can include information regarding diagnostics, performance, serial numbers, and/or other measuring device related information. Further, in an alarm mode, radiation detectors can be powered up and the radiation source strength measured. Further, in the event that a radiation source is stolen or missing, an alarm signal can be communicated to the central computer system.

In one embodiment, a measuring device can include an RFID system including a plurality of security layers having different levels of security and/or encryption. If a discrepancy is determined between a location of a measuring device and an associated predetermined route or boundary, a comparison between an actual route of the measuring device and a manifest from the RFID system can determine whether any action should be taken. An actual route can be determined from a locating device, such as a GPS system, located on or in proximity to the measuring device or another object such as radioactive material. The RFID system and GPS system can be integrated as one or multiple systems. Integrated RFID/GPS systems can be used in applications that GPS is an integral part of functionality. In one example, an RFID chip can be used that has been issued by the government and encrypted for authentication and privacy protection. In another example, checkpoints in a shipping and/or trucking depot can include a code for decryption at an associated security level. The encryption can include digital watermarking or holography embedded in data. For authentication, any suitable types of algorithms can be utilized.

The security level of an RFID can have a plurality of layers of encryption and authentication whereby different authorities can have different keys. For example, nuclear devices can be detected at a checkpoint. In this example, the first layer of encryption can be simply authenticating an operator of a vehicle transporting a measuring device and measuring device identification. If the operator is authenticated, transport of the measuring device can continue. If the operator is not authenticated, alarms can be generated for notifying proper authorities.

The integration of RFID systems into the operation of measuring devices can include providing a history of the operation of the measuring device. This could include past projects, locations, ownership and service records. An RFID system can also maintain position/location information of a measuring device, and underutilized equipment can be identified and relocated. In another example, an RFID system can provide smart labeling to a measuring device. In this example, information on the instrument model, serial number, its specifications, characteristics can be instantly read and imported into a spreadsheet if necessary. In another example, an RFID system can be utilized for authenticating the use of hazardous materials in a measuring device. In another example, RFID systems can provide calibration/repair encryption/authentication keys. In this application, the section of memory of the device that holds the calibration constants is blocked unless permission is granted with the proper digital keys. In another example, RFID systems can provide multiple serial numbers, or other identifiers, for a measuring device and/or a hazardous material. For instance, medical devices have many serial numbers including those of the radiological isotope, model number, NRC licenses and the like. In another example, RFID systems can provide a record of an expected chemical signature or an energy spectrum of a material. In another example, RFID systems can provide a shipping manifest and route. In another example, RFID systems can include identification information associated with an operator of a measuring device. RFID systems can include a public/private encryption/authentication key system. In another example, an RFID system can provide different encryption/authentication layers for different authorities.

In one embodiment, hazardous material can be associated with an RFID system for use in an electronic article surveillance (EAS) mode. In this application, a unique signature RFID tag can be associated with a hazardous material. A signpost or other suitable reading device can trigger when an RFID tag leaves a predetermined area. In response to the triggering, an alarm state can be activated passing information from the tag and notifying authorities according to the subject matter described herein. The position of the hazardous material can be sent to the authorities in the alarm state. In one example, an EAS system can include positioning two systems in communication with one another, one system on a transporter and one system on a measuring device including hazardous material. In the event that the two systems are separated by a predetermined distance, authorities can be notified according to the subject matter described herein. In another example, the EAS system can require proof of ownership or the authority to use a measuring device.

In one exemplary use in the hazardous material transportation industry, RFID and GPS systems can be used for tracking purposes in forensics and security of hazardous material. For security purposes, an RFID chip can be programmed with shipping information such as expected routes, points of contact, serial numbers, owner information, shipping manifests, shipping routes, and the identity of hazardous material. Ports of call can be configured to detect RFID information and the actual shipping route from the GPS system. Information stored in the RFID system can be used to identify the hazardous material. For example, if the hazardous materials are nuclear materials, an energy spectrum of the nuclear materials can be uploaded from the RFID system, and spectrum analysis techniques used to identify isotope(s) for verifying that the material matches the identification stored in the RFID system. Other hazardous materials, such as biological, gases, solid, and liquid materials, can be detected by suitable techniques such as optical, mass, infrared, or gas spectroscopy. In another example, millimeter waves can remotely detect or identify molecular signatures, as the frequency distribution resulting from an electromagnetic perturbation can be a material signature. Further, millimeter waves and terahertz radiation can be used to detect radiation-induced effects also remotely through reflection and scattering techniques.

Figure 15:
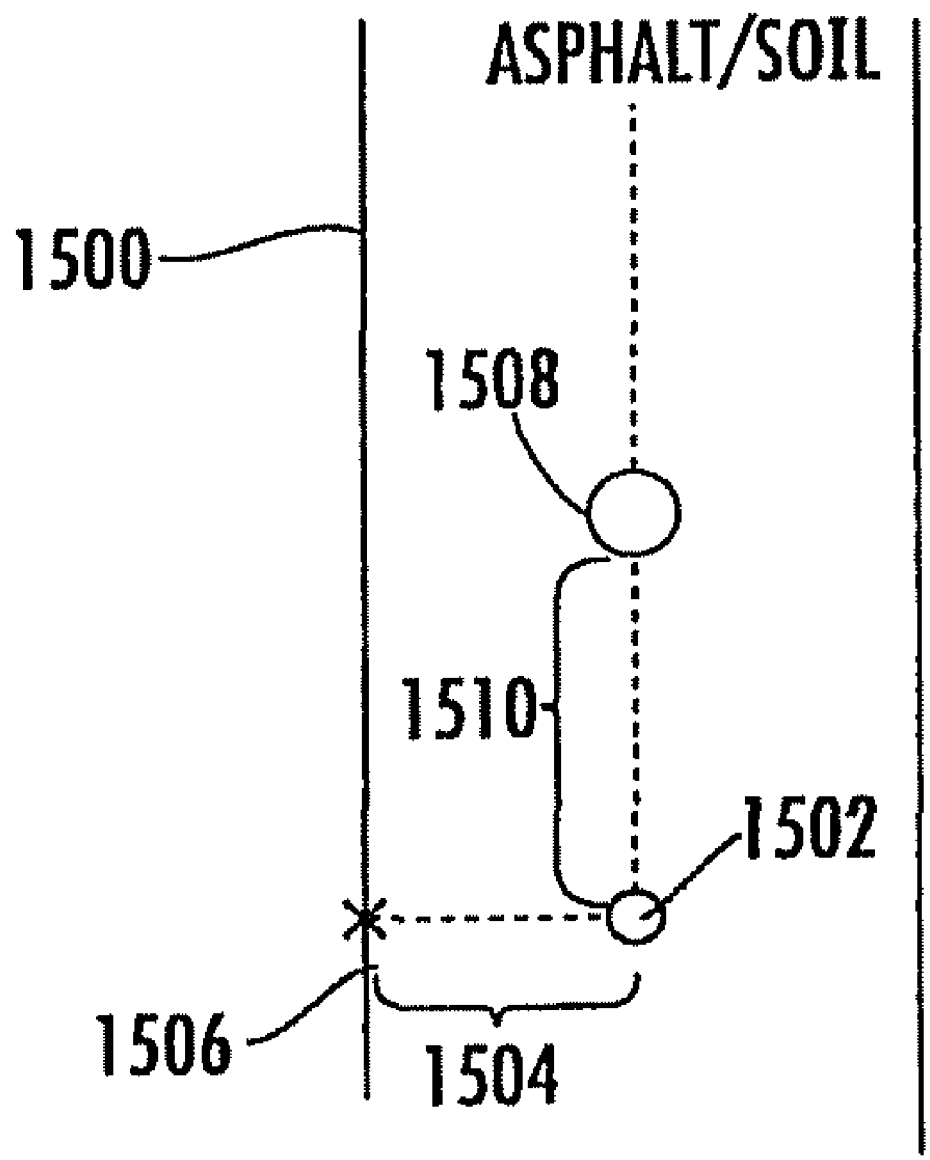
FIG. 15 is a top plan view of predetermined locations on an asphalt/soil surface for obtaining coring locations and measurements according to the subject matter described herein.

In one embodiment, the locating systems described herein can be applied to determining the locations of coring measurements. FIG. 15 illustrates a top plan view of predetermined locations on an asphalt/soil surface for obtaining coring measurements according to the subject matter described herein. Referring to FIG. 15, a plurality of core samples can be removed from asphalt/soil material 1500 in a predetermined pattern. A drilling device can be used for removing core samples in sequence from material 1500. For example, the drilling device can be used for removing a first core sample 1502 from material 1500. Sample 1502 can be removed at a position located at a predetermined distance 1504 from a starting position at an edge 1506 of material 1500. A second core sample 1508 can be removed at a position located at a predetermined distance 1510 from the location of removal of first core sample 1502. Other core samples can be removed at predetermined distances from each other. Here, a GPS system may be attached to the coring rig, or held in hand for marking positions for the operator. In this example the GPS can give vectors and directions to each coring location or the operator can core and mark the location as points of interest for the nuclear operators.

A gauge with core locations embedded in its memory or calculated from a starting point can be used to select where the nuclear gauge is placed for a nondestructive measurement. The measurement is made and recorded along with location, operator ID, time and date, and optionally, the gauge could produce a bar code or RF Tag containing measurement information that could be placed to mark the spot where the measurement was obtained. Alternatively, a wax pencil could mark an "X" at the measurement location. Next a coring tool comes and finds the spot either using the same GPS coordinates, by looking for a painted or marked "X" where "X marks the spot," sniffing out the RF tag, or looking for the barcode that was printed and stuck there from the gauge. Typically two cores are cut, one for the contractor, and one for the agency. They are measured by the water displacement system to verify that the nuclear gauge is in good agreement with the core. Nuclear offsets are sometimes made and then nondestructive nuclear measurements can be accepted as opposed to destructive drilling of cores. The same GPS coordinates from the gauge can be downloaded or linked to the drilling apparatus, and allow identification of the measurement spot to the drilling truck.

In one embodiment, a measuring device including a locating device as described herein can be used for determining predetermined distances between locations at which measurements are to be made and core samples are to be removed. Prior to core removal, an operator can move the measuring device along the surface of material 1500. The locating device can determine when the measuring device is a predetermined distance from the location of the coring procedure. When it is determined that the measuring device has been moved the predetermined distance, an indicator or alarm system can notify the operator that the measuring device is at the location. The operator can be notified of the location by viewing or following the display, hearing, or otherwise sensing the alarm. In response to the notification, the operator can proceed to the removal of another coring site, or another suitable measurement of material 1500 at the location. Further, the measuring device can be associated with a communications module operable to receive predetermined distances, positions or other suitable coordinate information for use in determining locations to obtain core samples from material 1500. Typically, the nondestructive measurement is made before the core is removed, and the core is drilled on or near the measurement spot.

Figure 16:
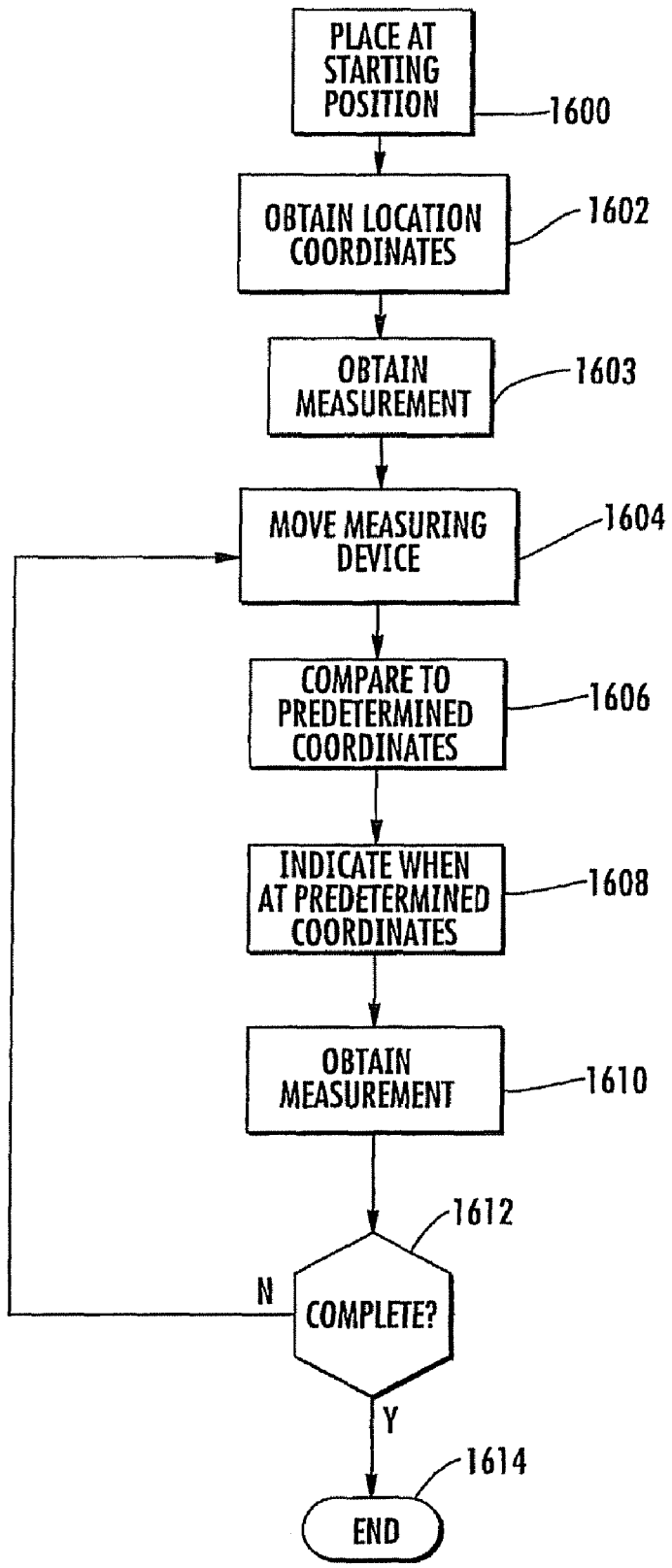
FIG. 16 is a flow chart of an exemplary process for positioning a measuring device for obtaining sample measurements and/or samples according to an embodiment of the subject matter described herein.

FIG. 16 illustrates a flow chart of an exemplary process for positioning a measuring device for obtaining sample measurements and/or samples according to an embodiment of the subject matter described herein. Referring to FIG. 16, the measuring device can be positioned at a starting position. For example, the measuring device can be positioned at an edge of a material surface or another suitable predetermined position (block 1600). In block 1602, the location coordinates at the starting position can be obtained. The measurement described with respect to FIG. 16 can be destructive or nondestructive, or marked with a bar code or tag. In block 1603, a sample measurement may be obtained.

In block 1604, the measuring device can be moved along a surface of the material. The position of measuring device during movement can be compared to predetermined locations for obtaining measurements (block 1606). When the measuring device is moved to one of the predetermined locations, the measuring device can indicate that the measuring device is at one of the predetermined locations (block 1608). A sample measurement can be obtained at the predetermined location (block 1610). In block 1612, the measuring device can determine whether the sample measurement session is completed. If it is determined that the session is not completed, the process can return to block 1604. Otherwise, if it is determined that the session is completed, the process can end at block 1614. A session may be determined to be completed when sample measurements have been obtained at all of the predetermined locations.

In one exemplary implementation of the subject matter described herein, location and identification information can be required for hazardous materials. An authorized hazardous material at a port should be identifiable. In one example, a spectrum-based system can be used as an identifier. In another example, a government-issued RFID tag with identification information can be used as an identifier. The identifier can be coded and/or encrypted if necessary. The need for identifiers is to reduce the harassment of legitimate citizens and their rights to operate safe equipment that may incorporate a material of regulation.

Hazardous material may be detected using microwave detectors, Raman-based systems, nuclear detectors, radiation detectors, FTIR systems, and/or mass spectroscopy for example. The detection may be in conjunction with the RFID tag and location information. The information can be compared to a government database for testing the legitimacy of the contents of the container. Tracking data can be used to determine that the material has left a port in a timely manner and tracked to a predetermined route. Inside a container, a portable micropower radar can be used to detect an intrusion into the container or its contents, the addition of contents to the container, and/or the removal of contents from the container or shifting of contents in the container that could result in damaging the goods. In one example, intrusion into a container can be detected by using a suitable motion detector. In another example, intrusion can be detected by radar. Other detection exemplary methods could be a change of pressure, aroma, strain gauge, acoustic, heartbeat detector, breathing detector, or simple the interruption of current in a trip wire.

Figure 17:
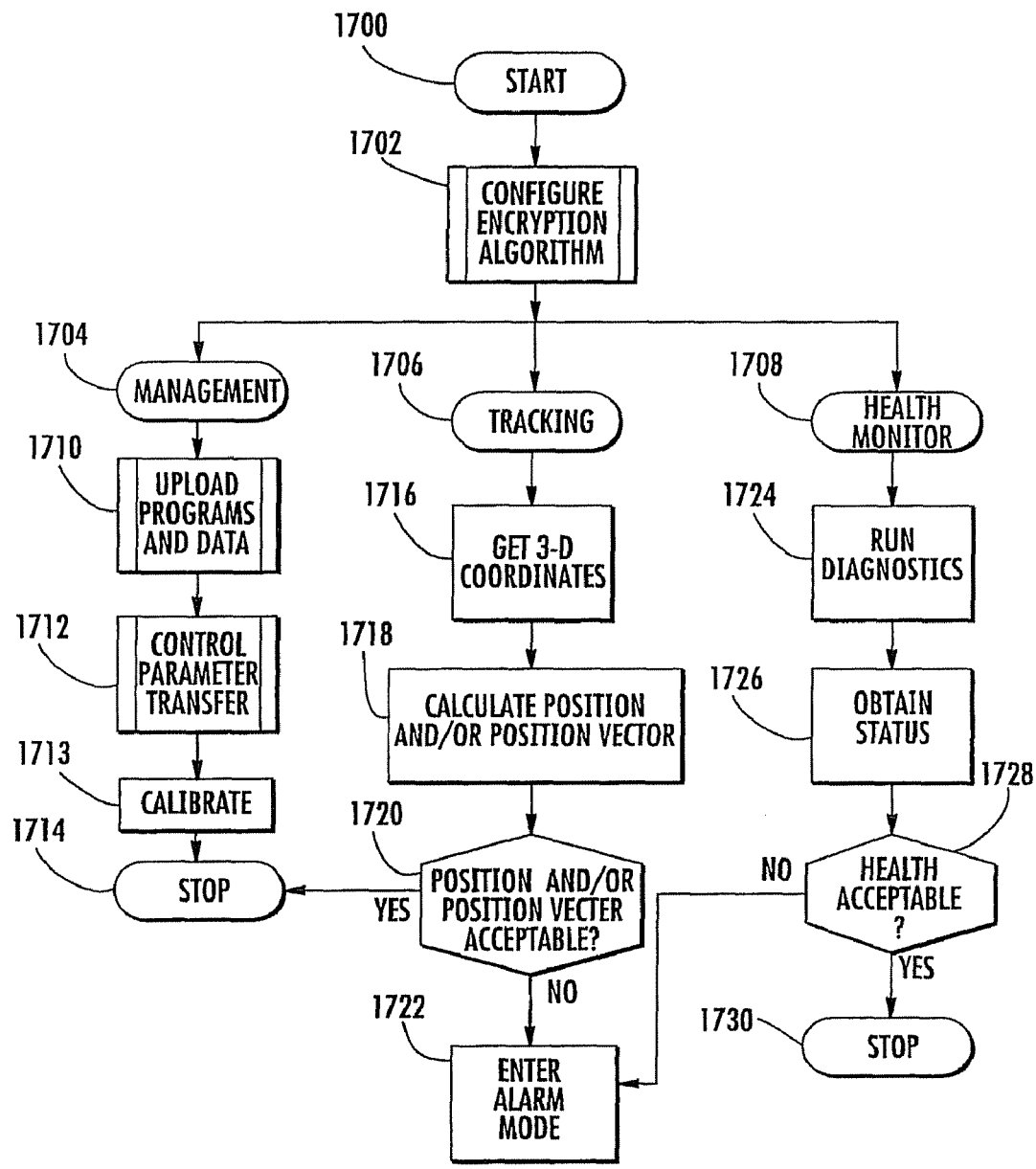
FIG. 17 is a flow chart of an exemplary process that can be implemented by a central computer system for controlling and monitoring a measuring device according to an embodiment of the subject matter described herein.

A central computer system can be configured to remotely control a measuring device and monitor the location and health of the measuring device. For example, central computer system 330 shown in FIG. 3 can be configured to remotely control and monitor a measuring device, such as measuring device 302. FIG. 17 illustrates a flow chart of an exemplary process that can be implemented by a central computer system for controlling and monitoring a measuring device according to an embodiment of the subject matter described herein. Referring to FIG. 17, the process can start at block 1700. Next, in block 1702, an encryption authentication algorithm for communicating with the measuring device can be configured. For example, the data and/or instructions communicated to the measuring device can be encrypted and keys passed. The data and/or instructions can be communicated to the measuring device by any suitable technique, such as some of the techniques described herein.

Next, the central computer system can enter a management mode 1704, a tracking mode 1706, or a health monitoring mode 1708. In management mode 1704, programs and data can be uploaded (block 1710). Programs such as updates for firmware that controls the communication module, tracking, locating, monitoring, graphics, tampering detection, user interface, measuring protocols and data such as an updated location of boundaries, location of measurements to be performed, and encryption/authentication keys. In block 1712, control parameters can be transferred to a measuring device. Control parameters can include measurement modes such as soil or asphalt, selection of special calibration curves, and instrument calibration programs. In block 1713, calibration and calibration check functions can be performed. Next, in block 1714, the process can stop.

In tracking mode 1706, three-dimensional coordinates of the measuring device can be obtained (block 1716). For example, the central computer system can communicate a request for coordinates to the measuring device. In response, a locating device can provide the coordinates. The coordinates can be communicated to the central computer system. Further, coordinates at different periods of time can be obtained and communicated to the central computer system. Based on the coordinates, the central computer system can calculate a position and/or position vector of the measuring device (block 1718). Next, in block 1720, the central computer system can determine whether the position and/or position vector of the measuring device is acceptable. For example, the position and/or position vector can be compared to a predetermined boundary, area, and/or route to determine whether the measuring device is at an acceptable position and/or moving in an acceptable direction with respect to the predetermined boundary, area, and/or route. If it is determined that the position and/or position vector is acceptable, the process can proceed to block 1714. Otherwise, if it is determined that the position and/or position vector is not acceptable, the central computer system can enter an alarm mode (block 1722). Setup of tracking modes, such as record only, real-time alarm mode, boundary, and/or curfew mode, can also be applied.

In the health monitor mode 1708, the central computer system can control a measuring device to run diagnostics (block 1724). Exemplary diagnostics can include verification of tamper proof processes, analysis of uptime, battery charge, precise locations logged in memory, calibration constant(s) verification, temperature and moisture/humidity values internal to the gauge, general electronic and software diagnostics to insure proper operation, verification of firmware updates and status. Next, in block 1726, the central computer system can obtain status information related to the diagnostics performed on the measuring device. The central computer system can determine whether the health of the measuring device is acceptable based on the status information (block 1728). If it is determined that the health is acceptable, the process can stop at block 1730. Otherwise, if it is determined that the health is not acceptable, the central computer system can enter an alarm mode (block 1722).

In one embodiment, all or a portion of the process described with respect to FIG. 17 can be used by any suitable device for controlling and/or monitoring a measuring device. Further, the data and/or instructions can be communicated to the measuring device by any suitable technique, such as some of the techniques described herein.

Figure 18:
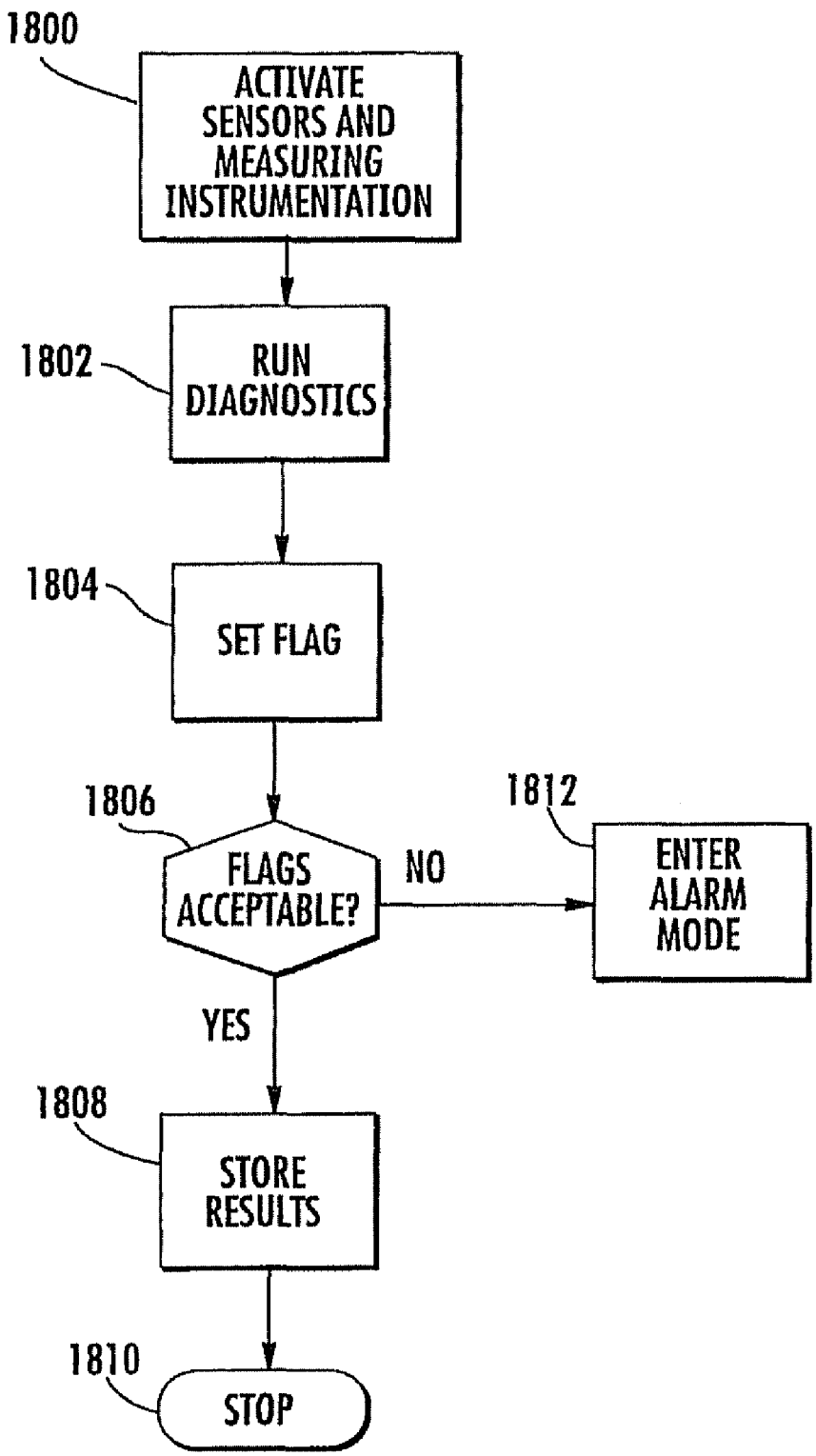
FIG. 18 is a flow chart of an exemplary process that can be implemented by a measuring device for health monitoring according to an embodiment of the subject matter described herein.

In one embodiment, a measuring device can be configured for health monitoring, storing results of the monitoring, and entering an alarm mode based on the monitoring result. FIG. 18 illustrates a flow chart of an exemplary process that can be implemented by a measuring device for health monitoring according to an embodiment of the subject matter described herein. Referring to FIG. 18, the measuring device can activate sensors and its measuring instrumentation (block 1800). In block 1802, diagnostics can be run for the sensors and measuring instrumentation of the measuring device. Flags can be set under predetermined conditions based on the diagnostics (block 1804). The flags can indicate one or more health conditions of the measuring device. Next, it is determined whether one or more of the flags are acceptable (block 1806). If the flags are acceptable, results can be stored in a database (block 1808) and the process can stop (block 1810). Otherwise, if the flags are not acceptable, the measuring device can enter an alarm mode (block 1812), which can notify an operator of the results and/or communicate signaling indicating the health monitoring results to a remote device, such as a central computer system.

Figure 19:
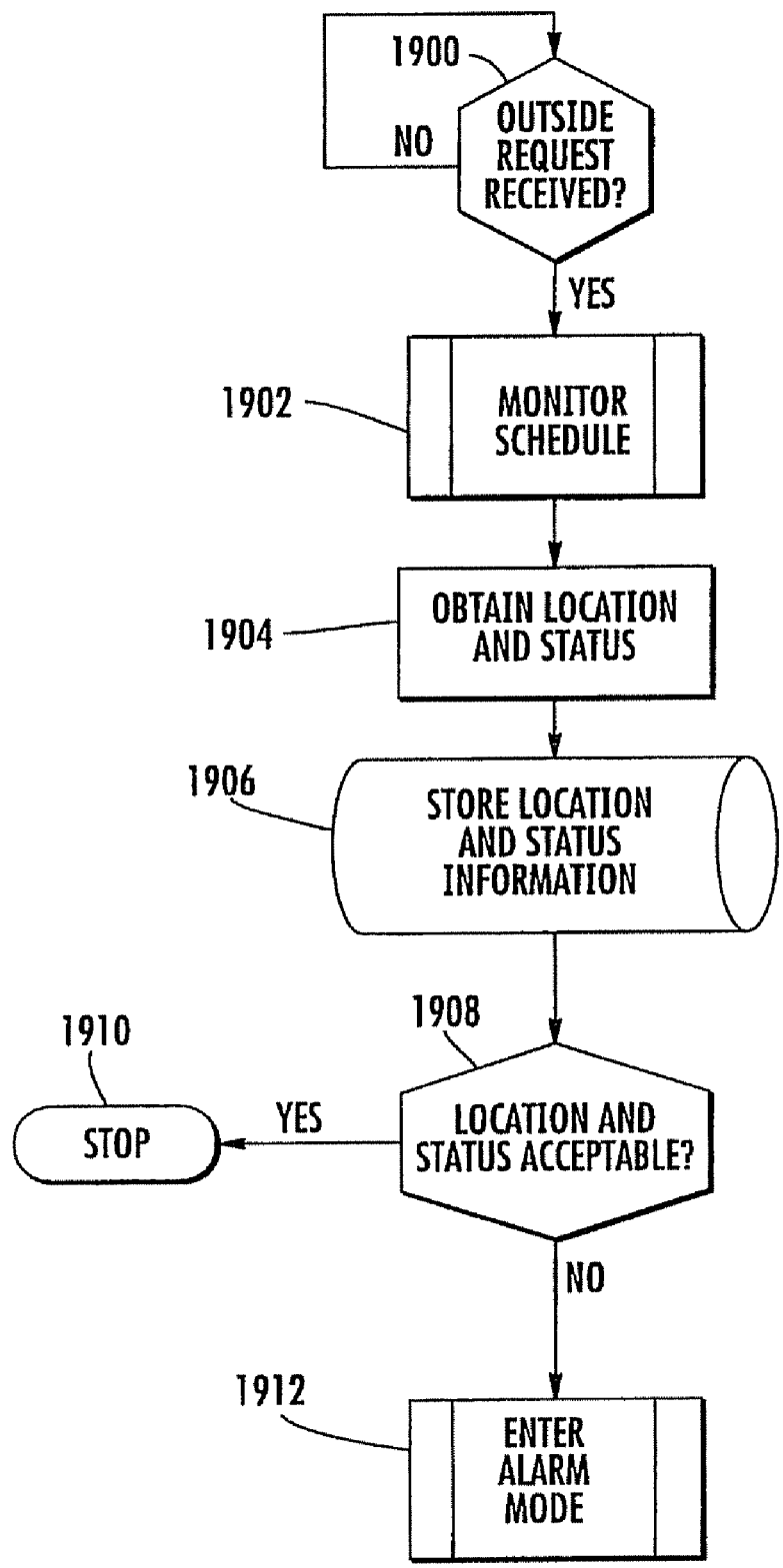
FIG. 19 is a flow chart of an exemplary process of monitoring location and status of a measuring device in a standalone system according to an embodiment of the subject matter described herein.

In one embodiment, the measuring device can be configured as a stand-alone system for monitoring location and status. FIG. 19 illustrates a flow chart of an exemplary process of monitoring location and status of a measuring device in a stand-alone system according to an embodiment of the subject matter described herein. Referring to FIG. 19, measuring device can determine whether an outside request for location and/or status information has been received by a remote device or system (block 1900). For example, a central computer system, another measuring device, or any other suitable network-enabled device can communicate a signal to measuring device for requesting location and/or status information. If it is determined using authentication and encryption protocols that a request has been received, the measuring device can implement a monitoring schedule for monitoring its location and status (block 1902). Alternatively, if it is determined that no request has been received, control may return to block 1900 where measuring device can re-attempt to determine whether an outside request for location and/or status information has been received by a remote device or system. In block 1904, the measuring device can obtain location and status information. The location and status information can be stored in a database associated with the measuring device (block 1906).

In block 1908, the measuring device can determine whether the location and status is acceptable based on predetermined criteria. The predetermined criteria can include predetermined routes, areas, locations, instrumentation, and other detected information associated with the measuring device. If it is determined that the location and status is acceptable, the process can stop (block 1910). If it is determined that the location and status is not acceptable, the measuring device can enter an alarm mode (block 1912). In the alarm mode, a remote device that communicated the request, another remote device, and/or an operator of the measuring device can receive information associated with the location and status information.

Figure 20A:
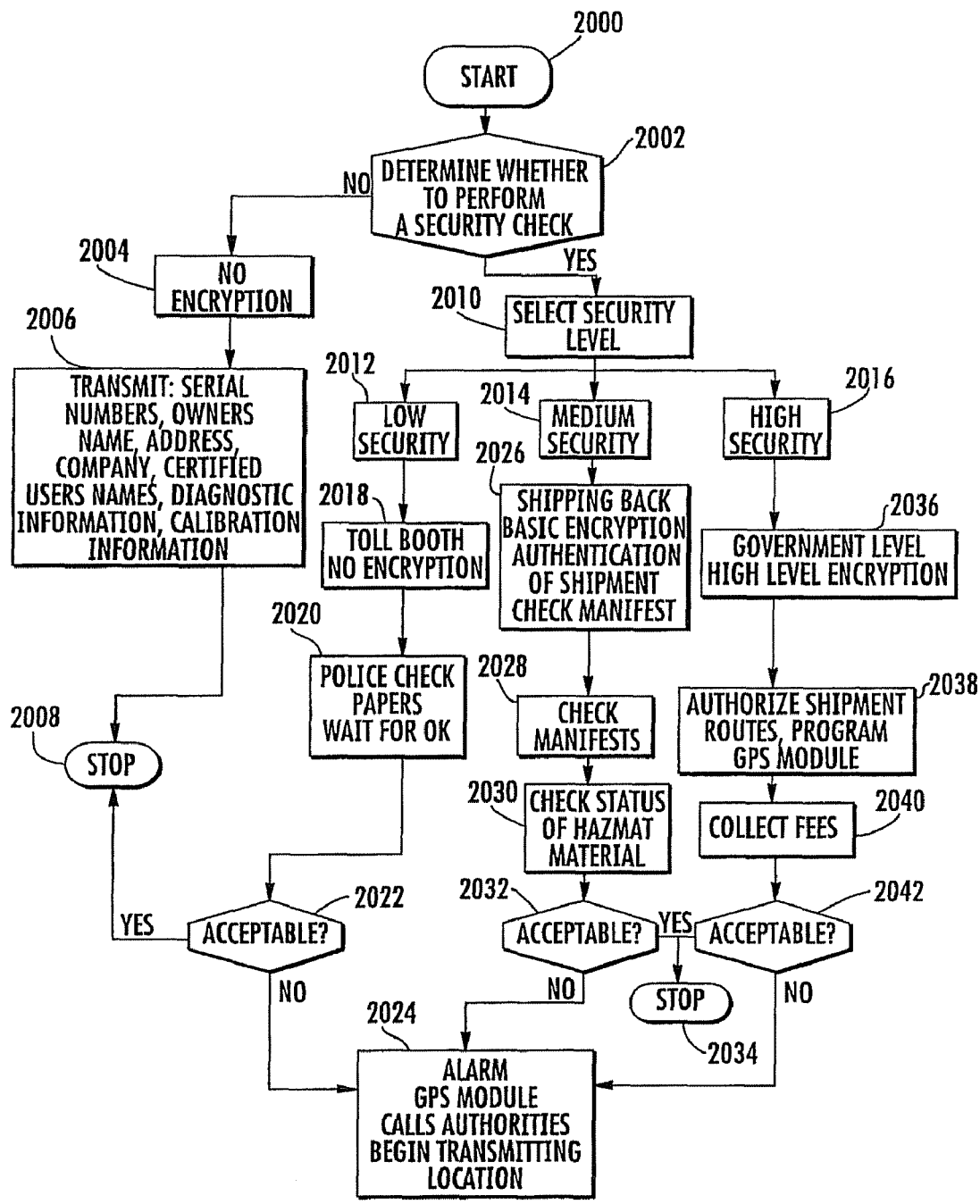
FIG. 20A is a flow chart of an exemplary process of the operation of a standalone or integrated RFID system of a measuring device at different levels of security and encryption according to an embodiment of the subject matter described herein.

FIG. 20A illustrates a flow chart of an exemplary process of the operation of an RFID system of a measuring device at different levels of security and encryption/authentication according to an embodiment of the subject matter described herein. Referring to FIG. 20A, the process can start at block 2000. Next, in block 2002, the RFID system can determine whether to perform a security check. If it is determined that a security check is not performed, the RFID system disables encryption (block 2004) and communicates information associated with the measuring device to a remote device (block 2006). The information is communicated in an unencrypted format. Exemplary information associated with the measuring device include serial numbers, owner name, address information, company name, identification of certified users, some diagnostic information, some calibration information, and any other related measuring device information. The process can stop at block 2008.

Referring again to block 2002, if it is determined that a security check is performed; a security level can be selected (block 2010). A low security level (in block 2012), a medium security level (in block 2014), or a high security level (in block 2016) can be selected. In low security level (block 2012), no or some encryption is provided for communicated information. In one example, the information can be provided at a toll booth (block 2018) and the measuring device and associated transportation waits at the toll booth (block 2020). It is determined whether the information is approved in block 2022. If approved, the process can stop at block 2008. Otherwise, the measuring device can enter an alarm mode (block 2024) in which the measuring device can communicate location information and/or status information to a remote device as described herein.

In medium security level (block 2014), the measuring device performs a predetermined basic encryption for authentication of shipment of the measuring device at a shipping dock and checks the manifest (block 2026). In block 2028, manifests are checked. Next, in block 2030, a status of any hazardous materials is checked. In block 2032, it is determined whether the manifest check and hazardous materials check are acceptable. If acceptable, the process can stop at block 2034. Otherwise, if not acceptable, the measuring device can enter an alarm mode (block 2024).

The medium security modes can be encrypted using a standard protocol or algorithm. Here, items such as management and maintenance data can be accessed. Medium security may allow for read/write, aid in organizing returns, equipment exchanges, warranty information, and maintaining inventory. In one embodiment, an employee may scan a card for access to thereby obtain information such as links to approved customer lists, customer IDs, jobsites, service intervals, and identify instrument build information or kits. These features may be accessed remotely via a web browser.

In a high security mode (block 2016), the measuring device performs a predetermined high level of encryption for government level authentication (block 2036). In block 2038, shipment routes can be authorized and the measuring device programmed with the shipment routes. Next, in block 2040, any fees associated with shipping can be collected. In block 2042, the measuring device can determine whether configuration and information associated with the high security mode operation is acceptable. If acceptable, the process can stop at block 2034. Otherwise, if not acceptable, the measuring device can enter an alarm mode (block 2024). Fees can be collected at any point in this exemplary process, not just in block 2040. High security encryption may allow read/writes and allow the setup of shipping information routes, boundary zones, alarm status, and change of ownership of instrument or material. These features may be accessed remotely via a web browser.

Figure 20B:
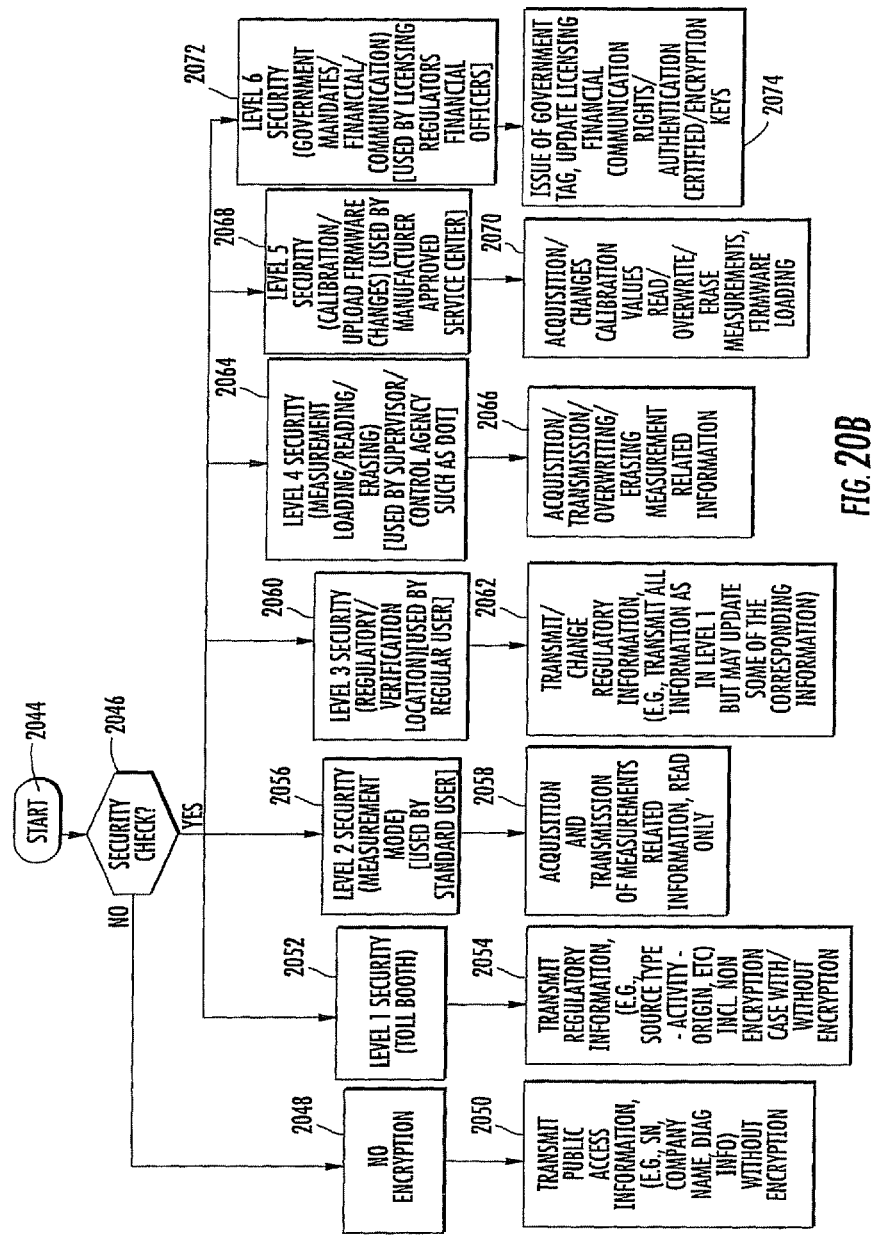
FIG. 20B is a flow chart of an exemplary process for checking security of a measuring device, an object comprising hazardous material, or any other object according to an embodiment of the subject matter described herein.

FIG. 20B is a flow chart illustrating an exemplary process for checking security of a measuring device, a container including hazardous material, or any other object according to an embodiment of the subject matter described herein. Referring to FIG. 20B, the process begins at block 2044. At block 2046, a security check is performed, where it is determined the level of security required and whether encryption is required. If it is determined that no encryption is required, the process proceeds to a no encryption state at block 2048. Next, the process proceeds to block 2050, where public access information may be transmitted. Examples of public access information include a serial number for a device, a company name, and diagnostic information. This type of information can be transmitted without encryption. Further, the information may be stored on an RFID tag or other suitable memory.

In this example, six levels of security may be available. The security levels include: Level 1 Security, Toll Booth; Level 2 Security, Measurement Mode; Level 3 Security, Regulatory/Verification Location; Level 4, Measurement Loading/Reading/Erasing; Level 5 Security, Calibration/Upload Firmware Changes and Hardware Enable and Factory Maintenance, to be used by authorized repair facility; and Level 6 Security, which could be government mandated information or fee collection, tracking and boundary setups, authorization of reporting addresses. The levels of security can be obtained using a single or a plurality of encryption keys, authentication certificates, and encryption-authentication algorithms. For example, a given level of security may be reached using a key and/or certificate. A second level of security may require a different key, whose number of bits may be higher than the previously mentioned level. A third level of security may need the combination of both keys/certificates from the first and second levels as well as a third key/certificate.

At block 2046, if it is determined that Level 1 Security is required, the process proceeds to block 2052 for a Level 1 Security state. Level 1 security may be required when a vehicle transporting the object is stopped at or near a toll booth. In this case, at block 2054, regulatory information may be transmitted either encrypted or not encrypted. Examples of the regulatory information include source type, activity relating to the object, and point of origin.

At block 2046, if it is determined that Level 2 Security is required, the process proceeds to block 2056 for a Level 2 Security state. Level 2 security may be required when a measurement is acquired, and location information relating to the measurement should be transmitted. In this case, at block 2058, measurement and location tracking information stored in the device may be transmitted.

At block 2046, if it is determined that Level 3 Security is required, the process proceeds to block 2060 for a Level 3 Security state. Level 3 security may be required when an operator handling the object is required by regulations to verify location of the object. In this case, at block 2062, the same information transmitted in block 2054 may be transmitted. Some of the corresponding information may be updated.

At block 2046, if it is determined that Level 4 Security is required, the process proceeds to block 2064 for a Level 4 Security state. Level 4 security may be required when a certified operator from a regulatory or state agency needs to access the measurement and location tracking information and also need to reset, overwrite, erase measurement and location tracking information. In this case, at block 2066, the measurement and location tracking information may be transmitted and these pieces of information may be overwritten and erased. However, other sensitive information may not be altered at this level of security.

At block 2046, if it is determined that Level 5 Security is required, the process proceeds to block 2068 for a Level 5 Security state. Level 5 security may be required when the device requires calibration to guarantee proper performance and to maintain compliance to industry standards and regulations. In this case, at block 2070, the operator may be able to retrieve, change, erase the calibration values, and/or the measurement information. Further, the device may require updating or upgrading of the firmware, and/or repair, service, update, or change of mechanical, physical content or configuration. The operator may be able access, overwrite, write, or erase parts or the entirety of information stored inside the device. Some or all encryption keys and authentication certificates may be erased and/or changed. This level may be utilized by factory authorized service and manufacturing.

At block 2046, if it is determined that Level 6 Security is required, the process proceeds to block 2072 for a Level 6 Security state. Level 6 security may be required when governmental regulations require all or additional information regarding the objects manifest, contents, mandated information or the collection of fees. In this case, at block 2074, authorized personnel and receiving stations can be defined and financial charges obtained. Further, this level may require a master key where 2 or more parties could be required to access the information. For example, a government entity and a factory representative may hold keys necessary for access. Alternatively, Level 6 may be linked to the hardware/firmware definitions of the object, or be entirely dedicated to government needs and endorsements. Some or all of the encryption keys and authentication certificates may be updated, renewed and/or cancelled/erased.

Figure 21:
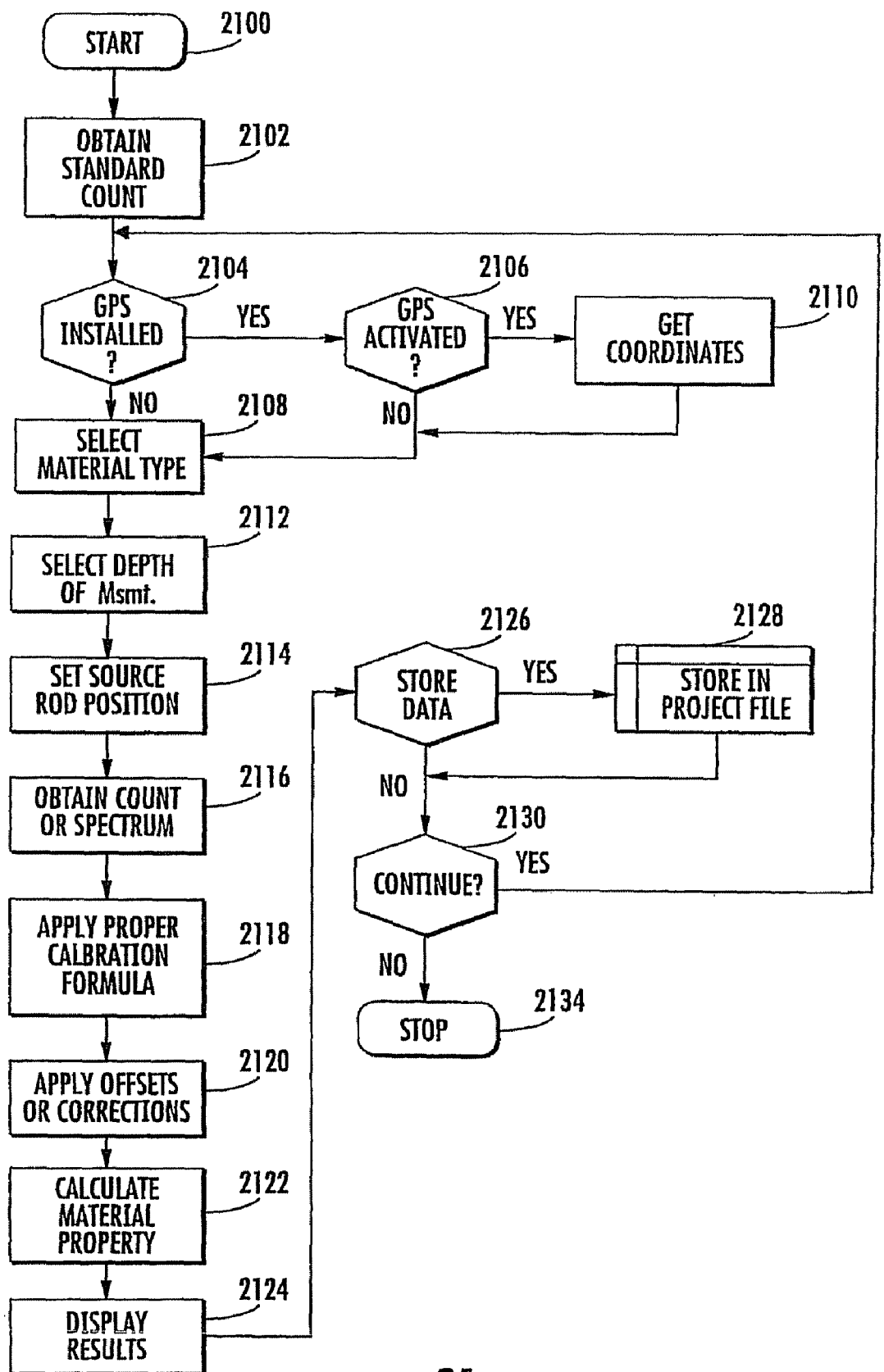
FIG. 21 is a flow chart of an exemplary process for obtaining a property measurement of a material and determining a location of the material in accordance with the subject matter described herein.

FIG. 21 is a flow chart illustrating an exemplary process for obtaining a property measurement of a material and determining a location of the material in accordance with the subject matter described herein. In one example, the process may be implemented by use of a measuring/locating/tracking device, such as the devices shown in FIGS. 2A and 2B. Referring to FIG. 21, the process begins at block 2100. At block 2102, a standard count is obtained. Next, at block 2104, it is determined whether GPS is installed. If it is determined that GPS is installed, it can be determined whether the GPS system of the device is active (block 2106). Otherwise, if it is determined that GPS is not installed, the process can proceed to block 2108.

At block 2106, if it is determined that the GPS is activated, coordinates obtained using the GPS are acknowledged (block 2110), and the process proceeds to block 2108. If it is determined that the GPS is not activated, the process proceeds directly to block 2108.

At block 2108, a material type is selected. This may be based on soil type or classification, or the aggregate and mix design of asphalt. Next, a depth of measurement can be selected (block 2112). A source rod can be positioned with respect to a material (block 2114), and a count or spectrum can be obtained along with the appropriate data analysis (block 2116). A proper calibration formula can be applied which is usually directly related to the characteristics of the material under test (block 2118). Further, offsets or corrections can be applied (block 2120). The material property can then be calculated after the material specific corrections or offsets have been applied (blocks 2120 and 2122). Further, the results can be displayed to an operator (block 2124).

In block 2126, it is determined whether data should be stored or transferred. If the data should be stored, the data is accumulated in a project file (block 2128) and the process proceeds to block 2130. If the data should not be stored, the process proceeds to block 2130. At block 2130, it is determined whether the process should continue, as the operator may need to obtain more measurement locations. If the process should continue, the process proceeds to block 2104. Otherwise, the process stops at block 2134.

In a work environment, standard counts may be initiated at the beginning of the day. This is a measurement taken with the source in a standard position whereby the gauge is placed on a standard block at the testing site. For actual measurements, the standard count may be ratioed with the measurement count and this ratio determines the property of the material. Using ratios significantly reduces day to day drift of an instrument and the systematic inaccuracies that could be the result of the environment.

The process of obtaining a property measurement of a material and determining a location of the material described with respect to FIG. 21 is only one example. Many other variations of the process may be utilized. In particular, any of the steps of the process may be rearranged in any suitable order for achieving property measurements and determining locations.

Figure 22:
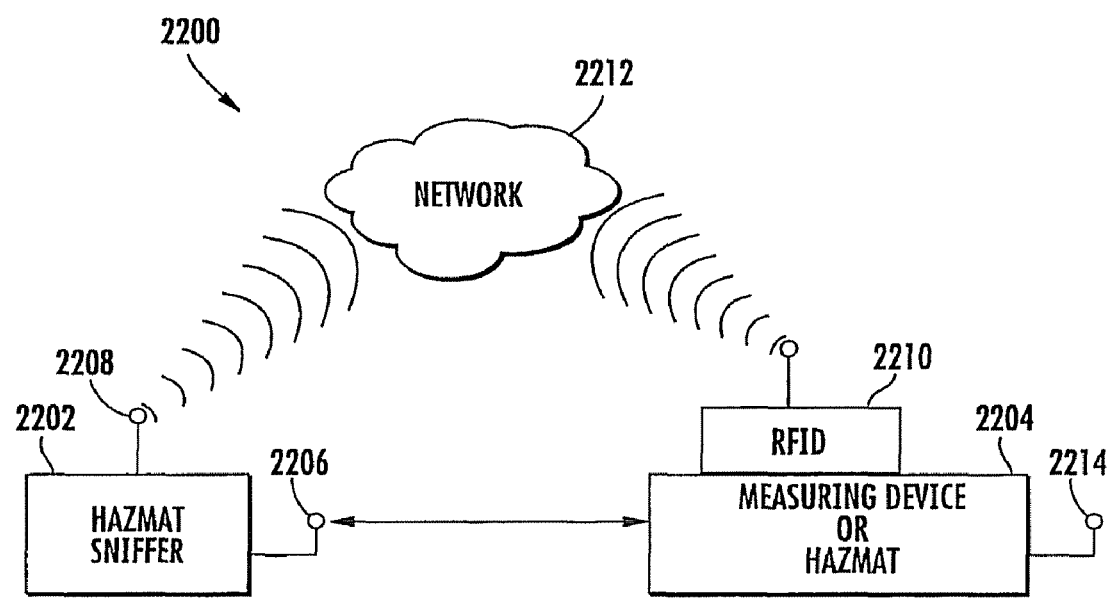
FIG. 22 is a block diagram of a measuring device/hazmat detection system according to an embodiment of the subject matter described herein.

FIG. 22 is a block diagram of a measuring device for hazardous material detection, and is a system generally designated 2200 according to an embodiment of the subject matter described herein. Referring to FIG. 22, system 2200 may include a detection device 2202 operable to detect the contents of an object 2204 containing a hazardous material. Device 2202 may include a detector 2206 configured to detect the hazardous material of object 2204. In other examples, detector 2206 may be a spectrum analyzer, or an XRF configured for sensing chemicals, or configured for sensing radioactive material, or configured to sense biohazards, liquids, gasses, poisonous materials and the like. Further, device 2202 includes an RFID reader/transceiver 2208.

Object 2204 may include an RFID chip 2210 operable to communicate via a wireless network 2212 or directly to RFID reader/transceiver 2208. The information can be suitable for encryption and two-way communication, between device 2202 and object 2204. Further, as a measuring device, device 2204 may also include a sensor or detector 2214 operable to measure materials, but is the object under investigation by device 2202 in this instance. In one example, object 2204 may comprise cargo or include devices having hazardous material, such as a nuclear gauge.

During operation, device 2202 can read the RFID library from RFID chip 2210 as to the contents or MSDS of object 2204. This data can include the expected measurement that detector 2206 will or has observed. In this example, the spectrum downloaded from RFID chip 2210 can be compared to information stored in the memory of device 2202, or transmitted from a central computer system via network 2212 or only the information that RFID chip 2210 transfers to RFID reader/transceiver 2208. When device 2202 activates the physical measurement of detector 2206, the actual measurement obtained should be compared to the expected library or data table sent from RFID chip 2210. If the measurement agrees with the MSDS or data, and all authoritative information is congruent, then there can be high confidence that the hazardous material is friendly, and further scrutiny may not be necessary.

It will be understood that various details of the subject matter described herein may be changed without departing from the scope of the subject matter described herein. Furthermore, the foregoing description is for the purpose of illustration only, and not for the purpose of limitation.

What is claimed is:

1. A system for locating and tracking an object, the system comprising:
   a measuring device configured to determine a property of a paving-related material, wherein the property includes at least one subsurface material property;
   a locating device configured to determine a location of the measuring device;
   a tracking system configured to store tracking information associated with the measuring device; and
   a communications system configured to transfer, to a remote device, the location of the measuring device and the tracking information associated with the measuring device.

2. The method of claim 1 wherein the locating device includes at least one of a geographic information system (GIS), a global positioning system (GPS), nationwide differential global positioning system (NDGPS), a high accuracy-nationwide differential global positioning system (HA-NDGPS), the European satellite system Galileo, global navigation satellite system (GLONASS), compasses, accelerometers, magnetometers, signpost components, dead reckoning components, wave propagating components, and RF components.

3. The system of claim 1 wherein the communications system includes one of a smart phone, a removable universal serial bus (USB)-based storage device, a wired connection, and a wireless connection.

4. The system of claim 1 wherein the measuring device is configured to measure at least one of a density, a density-related parameter, a temperature thermal property, a modulus, a stiffness, a texture, a moisture content, a surface texture of at least one of a soil, an aggregate, and an asphalt or cement paving mix.

5. The system of claim 1 wherein the locating device is configured to determine the location of the measuring device independently of the property measurement.

6. The system of claim 1 wherein the locating device is configured to determine the location of the measuring device when or about when the property of the paving-related material is determined.

7. The system of claim 1 wherein the measuring device is selected from the group consisting of a nuclear density gauge, a seismic pavement analyzer, a stiffness gauge, a falling weight deflectometer, a ground penetrating radar device, a radio frequency device, an electromagnetic device, a microwave device, an acoustic device, a moisture measuring device, an optical device, an Infrared device, and combinations thereof.

8. The system of claim 1 comprising an authenticated and encrypted memory storage for storing a time stamp being associated with at least one of the property of the paving related material and the location of the measuring device.

9. The system of claim 1 comprising a computing system configured for associating a time stamp with at least one of the property of the paving related material and the location of the measuring device.

10. The system of claim 1 wherein the communications system is configured to receive a polling signal associated with the object and configured to communicate the location of the object and tracking information associated with the object in response to receiving the polling signal.

11. A method for locating and tracking an object, the method comprising:
    determining, by a locating device, a location of a measuring device configured to determine a property of a paving-related material;
    determining, using the measuring device, a property of a paving-related material, wherein the property includes at least one subsurface material property;
    storing, by a tracking system, tracking information associated with the measuring device; and
    communicating, by a communications system, a signal to a remote computer device that identifies the location of the measuring device and includes the tracking information associated with the measuring device.

12. The method of claim 11 wherein the locating device includes at least one of a geographic information system (GIS), a global positioning system (GPS), nationwide differential global positioning system (NDGPS), a high accuracy-nationwide differential global positioning system (HA-NDGPS), the European satellite system Galileo, global navigation satellite system (GLONASS), compasses, accelerometers, magnetometers, signpost components, dead reckoning components, wave propagating components, and RF components.

13. The method of claim 11 wherein determining a location of an object includes determining the location of the measuring device independently of the property measurement.

14. The method of claim 11 wherein determining a location of an object includes determining the location of the measuring device when the property of the paving-related material is determined.

15. The method of claim 11 wherein the measuring device is selected from the group consisting of a nuclear density gauge, a seismic pavement analyzer, a stiffness gauge, a falling weight deflectometer, a ground penetrating radar device, a radio frequency device, an electromagnetic device, a microwave device, an acoustic device, a moisture measuring device, a thermal property measuring device, an optical device, an Infrared device, and combinations thereof.

16. The method of claim 11 comprising associating a time stamp with at least one of the property of the paving related material and the location of the measuring device.

17. The method of claim 11 comprising receiving a polling signal associated with the object, and comprising communicating the location of the object and tracking information associated with the object in response to receiving the polling signal.

18. A non-transitory computer readable medium having stored thereon computer executable instructions that when executed by the processor of a computer perform steps comprising:
    determining, using a locating device, a location of a measuring device that is configured to determine a property of a paving-related material;
    determining, using the measuring device, a property of a paving-related material, wherein the property includes at least one subsurface material property;
    storing, using a tracking system, tracking information associated with the measuring device; and
    transferring, using a communications system, the location of the measuring device and the tracking information associated with the measuring device to a remote device.

19. The computer readable medium of claim 18 wherein the locating device includes at least one of a geographic information system (GIS), a global positioning system (GPS), nationwide differential global positioning system (NDGPS), a high accuracy-nationwide differential global positioning system (HA-NDGPS), the European satellite system Galileo, global navigation satellite system (GLONASS), compasses, accelerometers, magnetometers, signpost components, dead reckoning components, wave propagating components, and RF components.

20. The computer readable medium of claim 18 wherein the object is a measuring device configured to determine a property of a paving-related material.

21. The computer readable medium of claim 18 wherein the measuring device is configured to measure at least one of a density, a density-related parameter, a moisture content of at least one of a soil, a texture, an aggregate, a thermal property, a modulus, a stiffness, and an asphalt paving mix.

22. The computer readable medium of claim 18 wherein determining a location of an object includes determining the location of the measuring device independently of the property measurement.

23. The computer readable medium of claim 18 wherein determining a location of an object includes determining the location of the measuring device when the property of the paving-related material is determined.

24. The computer readable medium of claim 18 wherein the measuring device is selected from the group consisting of a nuclear density gauge, a seismic pavement analyzer, a stiffness gauge, a falling weight deflectometer, a ground penetrating radar device, a radio frequency device, an electromagnetic device, a thermal property measuring device, a microwave device, an acoustic device, a moisture measuring device, an optical device, an Infrared device, and combinations thereof.

25. The computer readable medium of claim 18 comprising associating a time stamp with at least one of the property of the paving related material and the location of the measuring device.

* * * * *